US009545486B2

(12) United States Patent
Suzuki

(10) Patent No.: US 9,545,486 B2
(45) Date of Patent: Jan. 17, 2017

(54) SYRINGE

(71) Applicant: SUZUKEN COMPANY LIMITED, Nagoya-shi, Aichi (JP)

(72) Inventor: Ichiro Suzuki, Nagoya (JP)

(73) Assignee: SUZUKEN COMPANY LIMITED, Nagoya-shi (JP)

( * ) Notice: Subject to any disclaimer, the term of this patent is extended or adjusted under 35 U.S.C. 154(b) by 383 days.

(21) Appl. No.: 14/354,866

(22) PCT Filed: Oct. 26, 2012

(86) PCT No.: PCT/JP2012/077728
§ 371 (c)(1),
(2) Date: Apr. 28, 2014

(87) PCT Pub. No.: WO2013/065597
PCT Pub. Date: May 10, 2013

(65) Prior Publication Data
US 2014/0309594 A1  Oct. 16, 2014

(30) Foreign Application Priority Data

Oct. 31, 2011 (JP) ................. 2011-238210

(51) Int. Cl.
*A61M 5/32*   (2006.01)
*A61M 5/28*   (2006.01)
*A61M 5/315*  (2006.01)

(52) U.S. Cl.
CPC ............. *A61M 5/3271* (2013.01); *A61M 5/28* (2013.01); *A61M 5/315* (2013.01); *A61M 5/32* (2013.01);
(Continued)

(58) Field of Classification Search
CPC ...... A61M 5/3271; A61M 5/326; A61M 5/28; A61M 5/315; A61M 5/32; A61M 2005/3263; A61M 2005/3247; A61M 5/3202; A61M 5/3213; A61M 5/3216; A61M 5/322; A61M 5/3243; A61M 25/0618; A61M 25/0631
(Continued)

(56) References Cited

U.S. PATENT DOCUMENTS 5,292,314 A   3/1994 D'Alessio et al.
5,403,286 A   4/1995 Lockwood, Jr.
(Continued)

FOREIGN PATENT DOCUMENTS

DE    10009814 A1     9/2001
DE    102006041809 A1  3/2008
(Continued)

OTHER PUBLICATIONS

Jansen et al., JP11-110837, date of publication: Nov. 24, 1999.*

*Primary Examiner* — Manuel Mendez
(74) *Attorney, Agent, or Firm* — Birch, Stewart, Kolasch & Birch, LLP

(57) ABSTRACT

A syringe (1B) comprises: a syringe body (1C) including a plunger (32) to be operated for injection of a drug solution; a cylindrical needle cover (11B) housing an injection needle (100A); and a spring (18) held in a compressed state by the needle cover (11B). The needle cover (11B) has seats (153A) and (155B) in a pair that abut on corresponding opposite ends of the spring (18) to restrict the position of the spring (18). Pushing in the plunger (32) further after injection deforms the seat (155A) to release restriction on the spring (18). The spring (18) free from the restriction abuts on the syringe body (1C). This biases the needle cover (11B) to move the needle cover (11B) to a position where the injection needle (100A) is housed.

12 Claims, 14 Drawing Sheets

(52) U.S. Cl.
 CPC ...... *A61M 5/326* (2013.01); *A61M 2005/3247* (2013.01); *A61M 2005/3263* (2013.01)

(58) Field of Classification Search
 USPC .......................................... 604/192–198, 263
 See application file for complete search history.

(56) References Cited

U.S. PATENT DOCUMENTS

| | | | |
|---|---|---|---|
| 5,429,612 | A | 7/1995 | Berthier |
| 5,718,239 | A | 2/1998 | Newby et al. |
| 5,971,953 | A | 10/1999 | Bachynsky |
| 6,203,529 | B1 | 3/2001 | Gabriel et al. |
| 6,213,977 | B1 | 4/2001 | Hjertman et al. |
| 6,547,764 | B2 | 4/2003 | Larsen et al. |
| 6,986,760 | B2 | 1/2006 | Giambattista et al. |
| 2002/0026146 | A1 | 2/2002 | Jansen et al. |
| 2003/0060776 | A1 | 3/2003 | Heiniger |
| 2003/0078546 | A1 | 4/2003 | Jensen |
| 2003/0105430 | A1 | 6/2003 | Lavi et al. |
| 2003/0199822 | A1 | 10/2003 | Alchas et al. |
| 2005/0038392 | A1 | 2/2005 | DeSalvo |
| 2005/0131354 | A1 | 6/2005 | Tachikawa et al. |
| 2007/0142789 | A1 | 6/2007 | Fisher et al. |
| 2008/0077093 | A1 | 3/2008 | Gratwohl et al. |
| 2008/0195051 | A1 | 8/2008 | Graf et al. |
| 2010/0042047 | A1 | 2/2010 | Suzuki |

FOREIGN PATENT DOCUMENTS

| | | |
|---|---|---|
| JP | 3-139363 A | 6/1991 |
| JP | 5-337180 A | 12/1993 |
| JP | 6-31747 U | 4/1994 |
| JP | 11-319090 A | 11/1999 |
| JP | 2001-523485 A | 11/2001 |
| JP | 2002-172166 A | 6/2002 |
| JP | 2003-199828 A | 7/2003 |
| JP | 2004-535255 A | 11/2004 |
| JP | 2005-512690 A | 5/2005 |
| JP | 2008-532657 A | 8/2008 |
| JP | 2008-307237 A | 12/2008 |
| WO | 6-142204 A | 5/1994 |
| WO | WO 99/25402 A1 | 5/1999 |
| WO | WO 01/91837 A1 | 12/2001 |
| WO | WO 02/09797 A1 | 2/2002 |
| WO | WO 03/008023 A1 | 1/2003 |
| WO | WO 03/045480 A1 | 6/2003 |
| WO | WO 03/053499 A1 | 7/2003 |
| WO | WO 2008/072715 A1 | 6/2008 |
| WO | WO 2009/114762 A1 | 9/2009 |
| WO | WO 2009/154826 A2 | 12/2009 |
| WO | WO 2011/149455 A1 | 12/2011 |

\* cited by examiner

SYRINGE

TECHNICAL FIELD

The present invention relates to a syringe having a housing function for an injection needle.

BACKGROUND ART

Various types of syringes are used for medical practices in medical facilities such as hospitals. Plastic disposable syringes have become mainstream recently. A syringe of this type that is used most commonly has a removable cap covering an injection needle. Keeping the injection needle covered with the cap until injection is started can prevent injuries and the like due to needlestick accidents before they occur. Covering the injection needle with the cap after the injection can prevent needlestick accidents and the like to occur during disposal of the syringe. The injection needle might be contaminated with a virus or the like infecting a patient after the injection, so that needlestick accidents should be prevented reliably particularly in such a case.

A syringe having an automatic housing function for an injection needle (needle) has been suggested in recent years with the intention of preventing needlestick accidents and the like to occur after administration of injection. As examples, a suggested syringe includes a needle retaining member biased toward a retreated side with a coil spring in a compressed state, and a restricting member to restrict retreat of the needle retaining member (see patent literatures 1 and 2, for example). According to such a syringe, pushing in a plunger (injection piston) further after injection deforms or displaces the restricting member to release restriction. This makes the needle retaining member retreat to house an injection needle. As another example, a suggested syringe includes a needle retaining member biased toward a retreated side and a latch mechanism to restrict retreat of the needle retaining member (see patent literature 3, for example). According to this syringe, the latch mechanism is disengaged when injection is completed, thereby making the needle retaining member retreat to house an injection needle.

However, the aforementioned conventional syringe having the automatic housing function for the injection needle encounters the following problem. The needle retaining member retaining an injection needle is biased with the spring. Hence, for assembly of the needle retaining member, assembling work should be accompanied by compressing the spring gradually, so that favorable workability of assembly might become unfeasible.

CITATION LIST

Patent Literature

Patent Literature 1: JP H6-142204
Patent Literature 2: JP H5-337180
Patent Literature 3: Japanese Translation of International Application No. 2008-532657

SUMMARY OF INVENTION

Problems to be Solved by the Invention

The present invention has been made in view of the above conventional problems, and aims to provide a syringe having a housing function for an injection needle that assures favorable workability of assembly and achieves excellent productivity.

Means for Solving the Problems

A first aspect of the present invention is intended for a syringe, comprising: a syringe body including an injection needle, a solution chamber storing a drug solution, and an operational part to be operated in a certain direction to inject the drug solution stored in the solution chamber from the injection needle; a cylindrical needle cover housing the injection needle; and an elastic member held by the needle cover while being compressed in an axial direction of the injection needle. The needle cover has seats in a pair to restrict the positions of both end portions of the elastic member in the axial direction by making abutting contact with the both end portions of the elastic member. The elastic member is held in a gap between the seats in a pair. A seat being one of the seats in a pair is deformed in response to operation on the operational part in the certain direction performed after injection to release restriction on the position of one end portion of the elastic member. The one end portion of the elastic member is to abut on the syringe body side in response to the deformation of the seat to bias the needle cover, thereby moving the needle cover to a position where the injection needle is housed.

A second aspect of the present invention is intended for a syringe, comprising: a drug solution container that is filled with a drug solution and has a shape of a cylinder with a bottom; a closing member that closes an opening of the drug solution container in a manner movable in a boring direction of the cylindrical shaped drug solution container; and a needle housing unit that is attached to the closing member so as to allow the closing member to be pushed into the drug solution container. The needle housing unit includes: a substantially columnar retaining member with an injection needle projecting from one end thereof and a perforation needle projecting from the other end thereof; a first holder member provided with a first hollow portion having a bottom and with a first slider portion, the first slider portion holding the retaining member using at least two pillar-shaped parts, the at least two pillar-shaped parts extending from a bottom side of the first hollow portion along an opening direction of the first hollow portion, which is equivalent to an axial direction of the injection needle, the at least two pillar-shaped parts circumscribing an outer circumferential surface of the retaining member, the first holder member, provided with seats in a pair at two positions in the axial direction, holding an elastic member in a compressed state with each position of both end portions in the axial direction restricted by a corresponding seat of the seats in a pair; and a second holder member provided with a second hollow portion having a bottom, with a second slider portion, and with an attachment portion, the second slider portion holding the retaining member using at least two pillar-shaped parts, the at least two pillar-shaped parts extending from a bottom side of the second hollow portion along an opening direction of the second hollow portion, which is equivalent to the axial direction, the at least two pillar-shaped parts circumscribing the outer circumferential surface of the retaining member, the attachment portion being provided so as to extend along a bottom end of the second holder member for the closing member. The first holder member and the second holder member are rotatable relative to each other around the retaining member in a state where each pillar-shaped part in the first slider portion or the second slider portion holding the retaining member does not overlap with any of the pillar-shaped parts in the other slider portion in the axial direction. In a state where the pillar-shaped parts in the first slider portion and the second slider portion are arranged alternately around the retaining member, the first holder member and the second holder member are retractable in the axial direction through insertion of one of the holder members into the hollow portion in the other holder member, whereas in a state where distal end surfaces of the pillar-shaped parts in one of the first slider portion and the second slider portion face distal end surfaces of the pillar-shaped parts in the other slider portion, the first holder member and the second holder member are not retractable in the axial direction. When the first holder member and the second holder member holding the retaining member are retracted in the axial direction, the perforation needle penetrates through the closing member and projects inside the drug solution container, and the injection needle projects toward the outside. When the first holder member and the second holder member are retracted further in the axial direction after injection, a seat being one of the seats in a pair provided in the first holder member is deformed to release restriction on the position of one end portion of the elastic member. The one end portion of the elastic member abuts on the second holder member directly or indirectly in response to the deformation of the seat, thereby extending the first holder member and the second holder member in the axial direction so as to house the injection needle.

Advantageous Effects of the Invention

According to the syringe of the present invention, the elastic member placed in a compressed state in advance is held only by the needle cover or the first holder member. During assembly of the syringe, the needle cover or the first holder member can be handled while the elastic member is assembled in advance to the needle cover or the first holder member. This eliminates the need for elastically deforming the elastic member while a different component is assembled. Thus, the syringe of the present invention is less likely to cause reduction of efficiency of assembly as a result of presence of the elastic member necessary for achieving a housing function for the injection needle.

Thus, the syringe of the present invention has excellent properties that achieve a housing function for the injection needle without causing reduction of efficiency of assembly. Suppressing reduction of efficiency of assembly can prevent increase of product cost, so that a syringe to be provided has an advantageous aspect in terms of cost.

In one preferred aspect of the syringe of the present invention, the seat is formed of a bent part of a substantial hairpin shape projecting toward an inner circumferential side of the needle cover or the first holder member and the bent part is deformed by stretching so as to be substantially flattened, and the elastic member is released from the restriction on the position of the one end portion in response to the deformation of the bent part.

In this case, an extremely simple action of substantially flattening the bent part by stretching can become a trigger for housing the injection needle.

In one preferred aspect of the syringe of the present invention, the seat has a latch mechanism that maintains holding of the bent part until injection is finished, and releases the bent part from the holding when the operational part is operated in the certain direction after the injection.

In this case, the function of the latch mechanism can maintain the elastic member in a compressed state reliably until administration of injection is finished.

In the syringe according to the second aspect of the present invention, the needle housing unit can shift between an axially retractable state and an axially non-retractable state in accordance with the positions of the first and second holder members associated with the relative rotation. In the axially non-retractable state, distal end surfaces of the pillar-shaped parts in one holder member face distal end surfaces of the pillar-shaped parts in the other holder member, and the retraction in the axial direction is restricted with high reliability. In this state, the injection needle does not project toward the outside inadvertently, and therefore the occurrence of needlestick accidents can be prevented with high reliability.

When administering the injection, the needle housing unit is retracted in the axial direction by pushing one holder member into the other holder member. As a result, the perforation needle projects from the rear end of the needle housing unit in vicinity to the drug solution container, and the injection needle projects to the outside from the distal end of the needle housing unit. The perforation needle penetrates through the closing member and reaches the inside of the drug solution container. By pushing the entire needle housing unit into the drug solution container in this state, the closing member moves in the forward direction inside the drug solution container. This forward movement allows the drug solution to be injected from the injection needle.

Axially retracting the first and second holder members further after injection recovers elasticity of the elastic member. The first and second holder members extend in the axial direction in response to this recovery, thereby enabling housing of the injection needle. By rotating the first and second holder members thereafter relative to each other, distal end surfaces of the pillar-shaped parts in one holder member can face distal end surfaces of the pillar-shaped parts in the other holder member, so that the needle housing unit can be placed in an axially non-retractable state again.

The needle housing unit of the syringe according to the second preferred aspect of the present invention can be placed in the axially non-retractable state again after injection by rotating the first holder member and the second holder member relative to each other after extending the first holder member and the second holder member in the axial direction to positions where each pillar-shaped part in the first slider portion or the second slider portion does not overlap with any of the pillar-shaped parts in the other slider portion in the axial direction. The elastic member is a spring formed by winding a linear material for a spring into a coil shape. The elastic member is held by the first holder member while storing rotation elastic force to act in a rotation direction generated by turning the elastic member in a circumferential direction. If the elastic member is released from the restriction on the position of the one end portion, the elastic member abuts on a seat provided in the second holder member while storing the rotation elastic force entirely or partially. The elastic member shifts the needle housing unit into an axially non-retractable state by extending the first holder member and the second holder member in the axial direction until the first holder member and the second holder member become rotatable relative to each other and then by applying the rotation elastic force to rotate the first holder member and the second holder member relative to each other.

In this case, housing the injection needle can automatically place the injection needle in a state that disables second-time projection of the injection needle.

Examples of a member applicable as the aforementioned elastic member include, in addition to the aforementioned coil spring, a member made of an elastic material such as a rubber material and an actuator filled for example with compressed air.

The syringe according to the second preferred aspect of the present invention comprises a surrounding sleeve having a substantially cylindrical shape. The surrounding sleeve restricts a relative rotation of the first holder member and the second holder member around the retaining member in a state where the surrounding sleeve surrounds the first slider portion and the second slider portion. The needle housing unit is in the axially non-retractable state in a manufactured state, and can be placed in the axially retractable state by rotating the first holder member and the second holder member relative to each other around the retaining member during injection. The surrounding sleeve allows the relative rotation of the first holder member and the second holder member around the retaining member in the manufactured state, and restricts the relative rotation of the first holder member and the second holder member once the needle housing unit has shifted from the axially retractable state to the axially non-retractable state again after injection.

In this case, after the needle housing unit is placed in an axially non-retractable state after injection, the relative rotation of the first holder member and the second holder member can be restricted. Restricting this relative rotation can reliably prevent the first and second holder members from returning to the axially retractable state.

DESCRIPTION OF EMBODIMENT

An embodiment of the present invention will now be described in detail using the following working example.

Working Example 1

The present example relates to a disposable pre-filled syringe 1A (a syringe that is already filled with a drug solution). Specifics of this pre-filled syringe 1A will be described below with reference to FIGS. 1 to 17.

Figure 1:
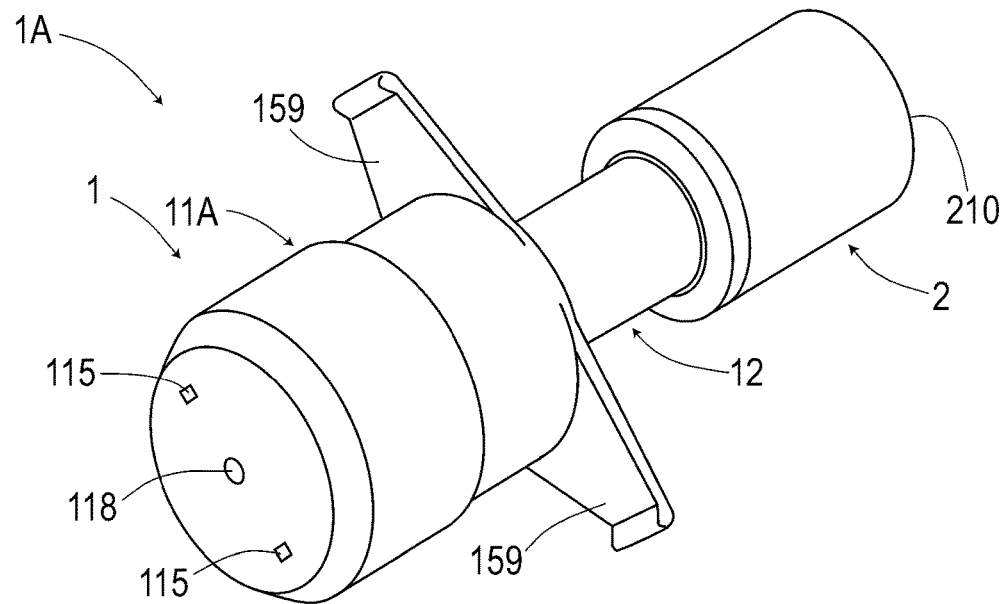
FIG. 1 is a perspective view showing a pre-filled syringe in a manufactured state according to a first working example.
Figure 2:
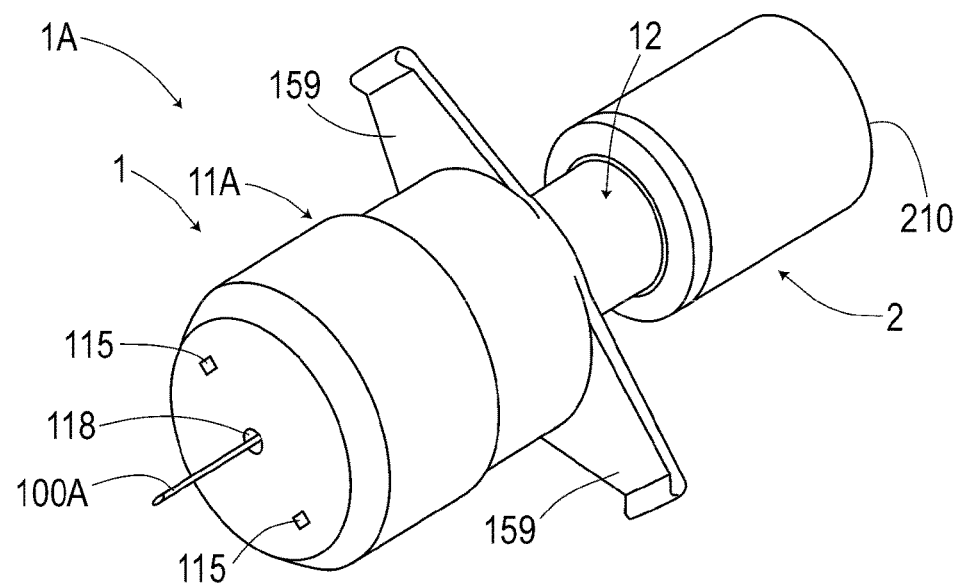
FIG. 2 is a perspective view showing the pre-filled syringe in an injection state according to the first working example.
Figure 3:
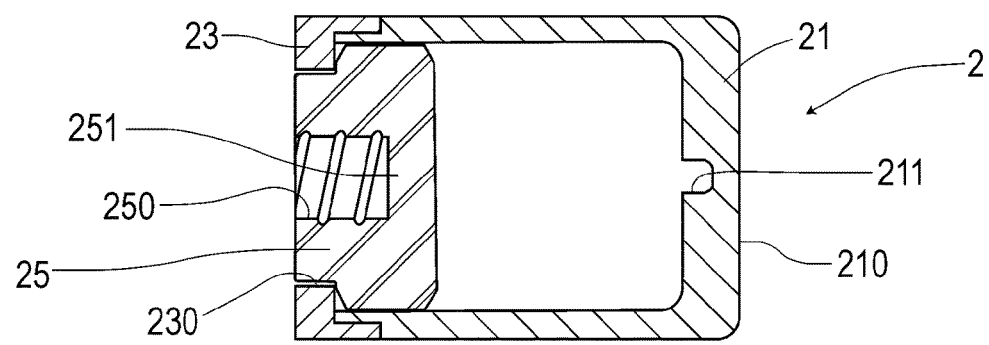
FIG. 3 is a cross-sectional view showing a cross-sectional configuration of a vial closed by a gasket according to the first working example.

As shown in FIGS. 1 to 3, the pre-filled syringe 1A according to the present example has a vial 2 (drug solution container), a gasket 25 (closing member), and a needle unit 1 (needle housing unit). The vial 2 has a shape of a cylinder with a bottom and is filled with the drug solution. The gasket 25 closes an opening in a manner movable in the boring direction of the cylindrical shaped vial 2 so as to push the drug solution out. The needle unit 1 is attached to the gasket 25. The pre-filled syringe 1A in a manufactured state has a total length of approximately 80 mm, and a maximum diameter of approximately 17 mm excluding finger grips 159. A syringe could be easy to handling in case the total length of approximately 60-100 mm and the maximum diameter of approximately 15-25 mm.

As shown in FIGS. 1 to 3, the vial 2 is a container having a shape of a cylinder with a bottom, and is to be filled with the drug solution. The vial 2 is closed by the gasket 25 inserted therein. A fall prevention portion 23 for preventing the gasket 25 from falling is attached to an open end of the vial 2. This fall prevention portion 23 has an opening 230 with a diameter smaller than the inner diameter of a body 21 of the vial 2. A recess 211 is bored on an inner bottom surface of the vial 2 to prevent reaching the perforation needle 100B (see FIG. 4) to the inner bottom surface.

As shown in FIG. 3, the gasket 25 is a substantially columnar member that is inserted into the vial 2 (body 21) and is made of butyl rubber or elastomer. This gasket 25 functions as a piston that moves in the forward direction toward the bottom side of the vial 2. An attachment hole 250 with a bottom is provided on an end surface of the gasket 25 that is exposed to the outside when the gasket 25 is inserted into the vial 2. A thread is provided on the internal circumferential surface of the attachment hole 250. The needle unit 1 is threaded into and attached to the attachment hole 250. The needle unit 1 can be attached to the gasket 25 by pressing into.

As shown in FIGS. 1, 2, and 4 to 6, the needle unit 1 is composed of a substantially columnar retaining member 10, a first holder member 11A, a second holder member 12, and a surrounding sleeve 13. An injection needle 100A and a perforation needle 100B project from both ends of the retaining member 10. The first holder member 11A and the second holder member house the retaining member 10 therein. The surrounding sleeve 13 is housed in the first holder member 11A and the second holder member while surrounding the outer circumferential side of the retaining member 10. It should be noted that the surrounding sleeve 13 is omitted from FIGS. 4 and 5, and the retaining member 10 is omitted from FIG. 6.

Figure 4:
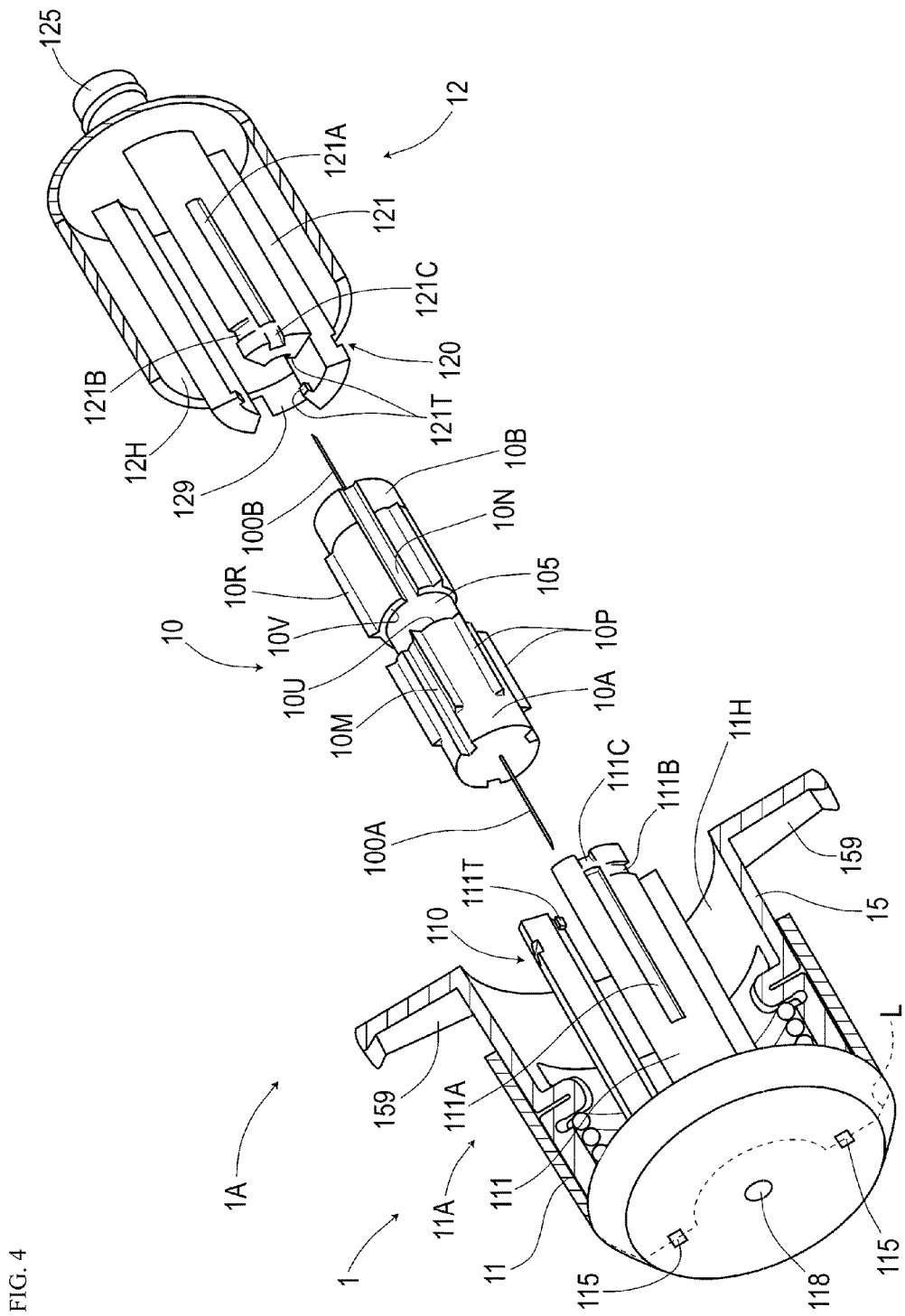
FIG. 4 is a perspective view showing an assembly configuration of a needle unit in the manufactured state according to the first working example.

As shown in FIG. 4, the retaining member 10 is a substantially columnar member made of polypropylene. A stainless steel tube 100 penetrates through the retaining member 10 along the central axis of the retaining member 10. This stainless steel tube 100 projects from both axial ends of the retaining member 10 and constitutes the injection needle 100A and the perforation needle 100B. The injection needle 100A on one side pierces through a site of injection, such as a human skin. The perforation needle 100B on the other side penetrates through the wall 251 in the gasket 25 (FIG. 3).

In the needle unit 1, the first holder member 11A and the second holder member 12 are coaxially joined via the retaining member 10. The needle unit 1 is retractable in the axial direction due to a configuration in which the second holder member 12 is inserted and housed in the first holder member 11A at the distal end side. Axially retracting the needle unit 1 with the vial 2 attached thereto allows the perforation needle 100B to project inside the vial 2 via the gasket 25, and allows the injection needle 100A to project toward the outside (see FIG. 2). By pushing the needle unit 1 into the vial 2 in this state, the gasket 25 moves in the forward direction, and therefore the drug solution can be injected from the injection needle 100A.

As shown in FIG. 4, the retaining member 10 according to the present example has a small-diameter portion 105, which is arranged at an axially intermediate portion thereof, between end surfaces 10U and 10V. A first shaft portion 10A and a second shaft portion 10B, which are substantially equal in diameter, are formed on both axial sides of the small-diameter portion 105. This retaining member 10 is assembled such that the first shaft portion 10A is located on the side of the first holder member 11A, and the second shaft portion 10B is located on the side of the second holder member 12.

As shown in FIG. 4, ridge portions 10P projecting toward the outer circumferential side are provided on the outer circumferential surface of the first shaft portion 10A at six places that are located at a substantially equal interval in the circumferential direction. Each ridge portion 10P extends along the axial direction. The outer circumferential surface of the first shaft portion 10A has six surface regions that are each arranged between the ridge portions 10P neighboring in the circumferential direction. Advance/retreat grooves 10M extending along the axial direction are provided in accordance with the same specifications on three of the six surface regions, more specifically, alternating surface regions out of the six surface regions.

As shown in FIG. 4, ridge portions 10R projecting toward the outer circumferential side are provided on the outer circumferential surface of the second shaft portion 10B at three places that are located at a substantially equal interval in the circumferential direction. Each ridge portion 10R extends along the axial direction. The outer circumferential surface of the second shaft portion 10B has three surface regions that are each arranged between the ridge portions 10R neighboring in the circumferential direction. Each of these three surface regions spans across approximately 120 degrees in the circumferential direction. Furthermore, advance/retreat grooves 10N extending along the axial direction are provided on the outer circumferential surface of the second shaft portion 10B at three places that are located at a substantially equal interval in the circumferential direction. Each advance/retreat groove 10N in the second shaft portion 10B is offset with respect to the corresponding advance/retreat grooves 10M in the first shaft portion 10A by approximately 60 degrees.

Figure 5:
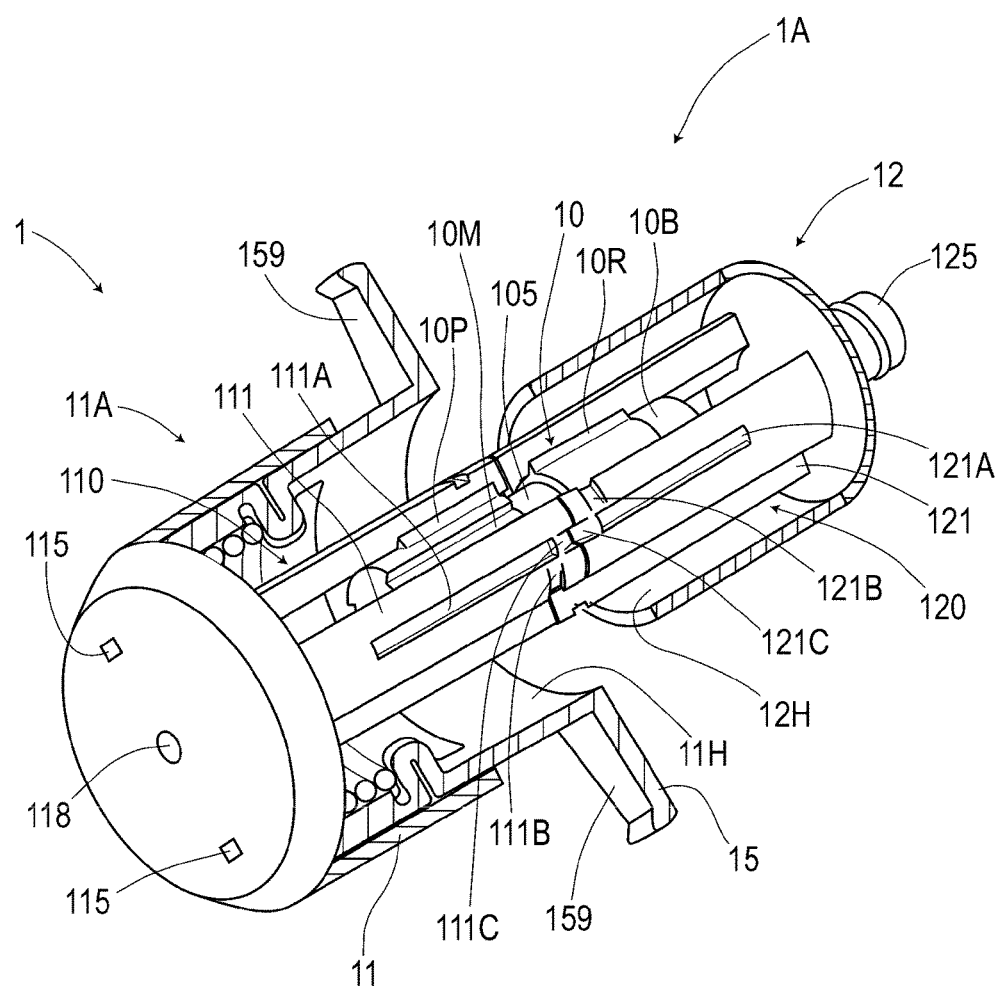
FIG. 5 is a perspective view showing the needle unit in the manufactured state according to the first working example.
Figure 6:
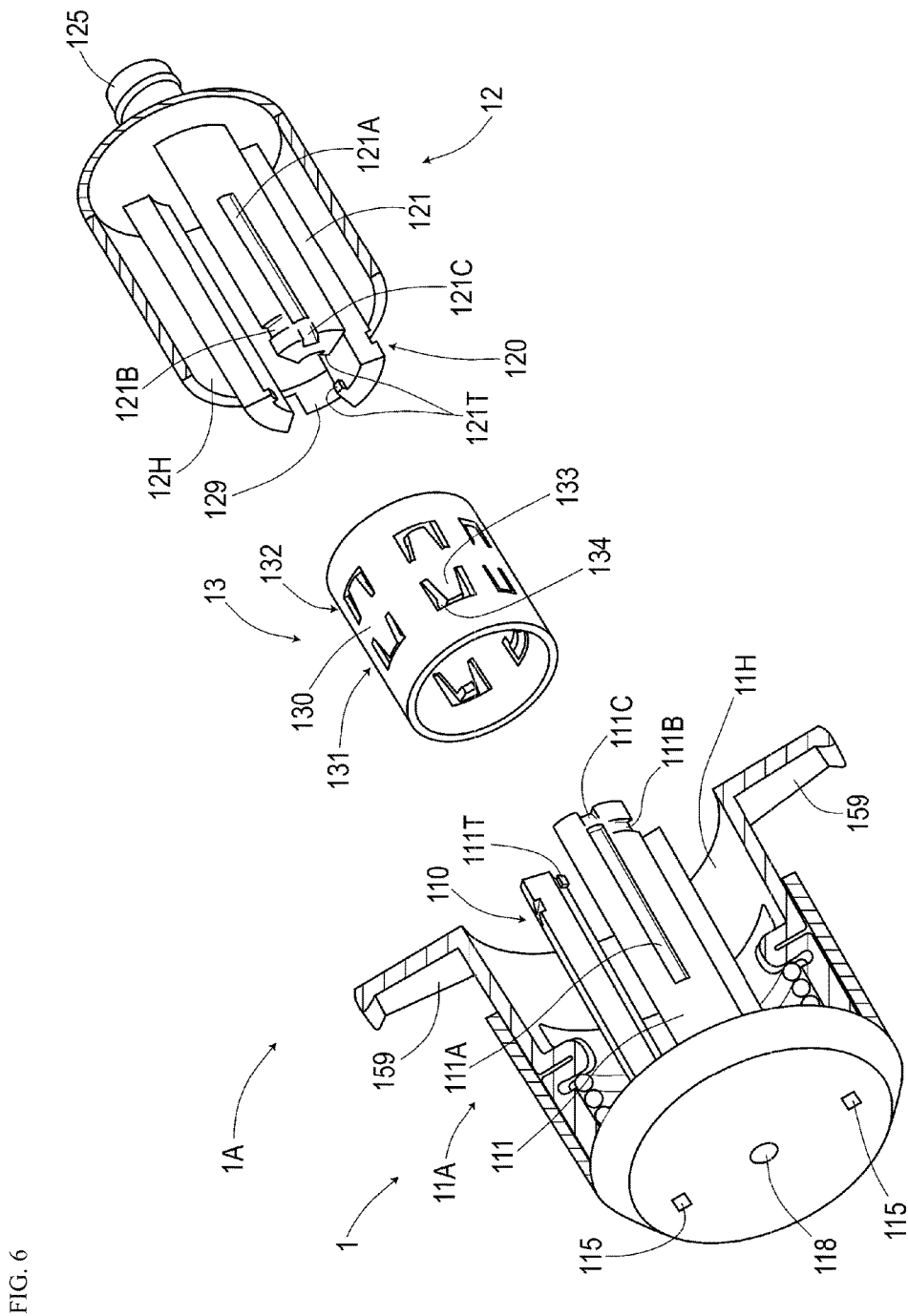
FIG. 6 is a perspective view showing the assembly configuration of the needle unit in the manufactured state according to the first working example.
Figure 7:
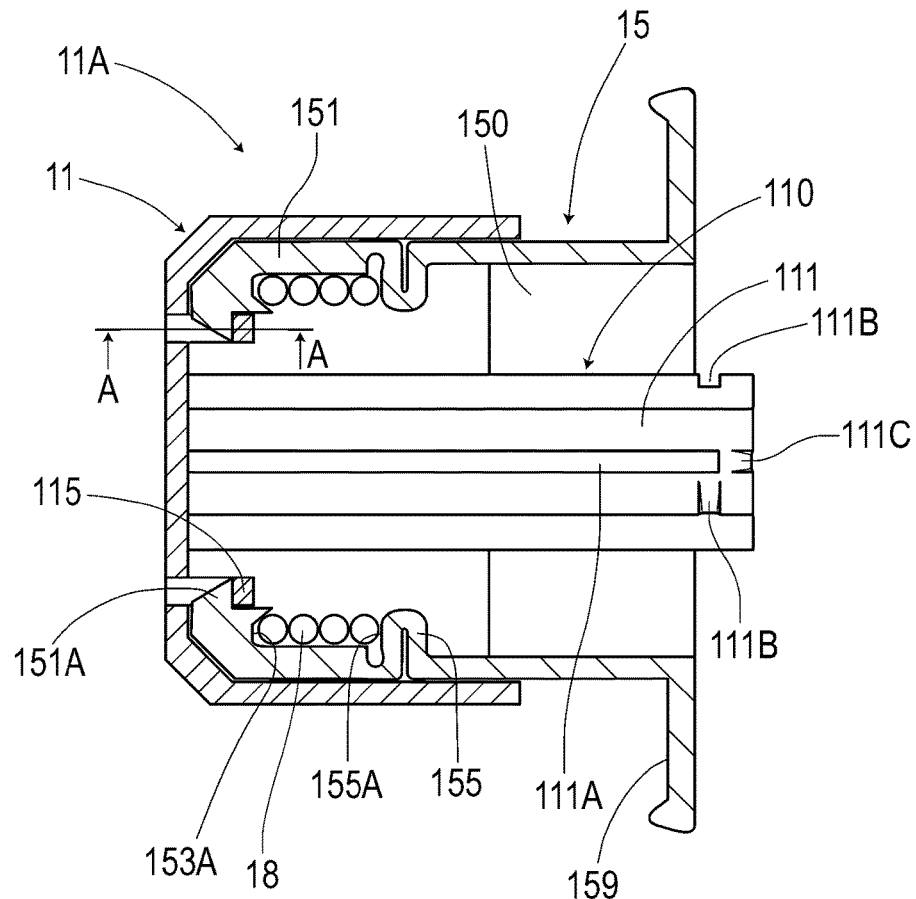
FIG. 7 is a cross-sectional view showing a cross-sectional configuration of a first holder member according to the first working example.
Figure 8:
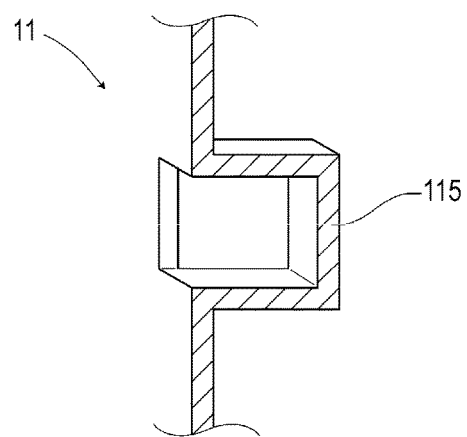
FIG. 8 is a cross-sectional view showing a clip part of the first holder member taken along line A-A indicated by arrows according to the first working example.

As shown in FIGS. 4 to 7, the first holder member 11A includes a combination of a holder body 15 and a cap 11 that are made of polypropylene. The holder member 11A entirely has a shape of a substantial cylinder with a bottom and is provided with the finger grips 159 in a pair at the open end of the first holder member 11A. The finger grips 159 are arranged at opposite positions so as to project toward the outer circumferential side. The holder member 11A is assembled in such a manner that the bottom side thereof is located at the distal end side of the pre-filled syringe 1A. A first hollow portion 11H, which is the internal space of the holder member 11A, has an inner diameter substantially equal to an outer diameter of the vial 2 within an extent that allows the vial 2 to be inserted into the first hollow portion 11H. A first slider portion 110 that can hold the retaining member 10 is provided in the first hollow portion 11H. FIG. 7 shows a cross section taken along dashed line L in FIG. 4.

The cap 11 surrounds an end portion of the holder body 15 opposite the finger grips 159. The cap 11 forms the bottom of the holder member 11A. A projection hole 118 from which the injection needle 100A projects is bored on the distal end surface of the cap 11 on the bottom side. Three pillar-shaped parts 111 forming the slider portion 110 stand on the inner bottom surface of the cap 11 so as to extend along the axial direction (a direction toward the open end) of the hollow portion 11H. The number of the pillar-shaped parts 111 may be two or four for example instead of three of the present example.

The three pillar-shaped parts 111 are all formed in accordance with the same specifications, and provided at three positions at an equal interval in the circumferential direction with the axis of the holder member 11A serving as the center. Locking parts 115 stand on the bottom surface of the cap 11 at positions in opposition to each other while the projection hole 118 is placed therebetween. The locking parts 115 are formed by punching process performed from the distal end side so as to hang down from the bottom surface in a substantially U shape (see FIG. 8). Clip parts 151A of the holder body 15 described later go into engagement with the locking parts 115.

As shown in FIG. 7, the holder body 15 has a cylindrical part 150 provided with the finger grips 159 and has a shape of a substantial cylinder, and holder posts 151 in a pair axially extending from the cylindrical part 150. The holder posts 151 in a pair are arranged in opposition to each other while the axis of the cylindrical part 150 serving as the center is placed therebetween. The holder posts 151 each have the clip part 151A at the distal end and a bent part 155 located at an intermediate portion. The clip part 151A is formed so as to project like a hook toward the inner circumferential side. In the holder body 15, the projecting shape of the clip part 151A defines a seat 153A of a spring 18. The bent part 155 is formed by being folded back toward the inner circumferential side so as to have a shape like the distal end shape of a hairpin. The bent part 155 forms a shelf surface that defines an opposite seat 155A of the spring 18 facing the seat 153A.

Figure 9:
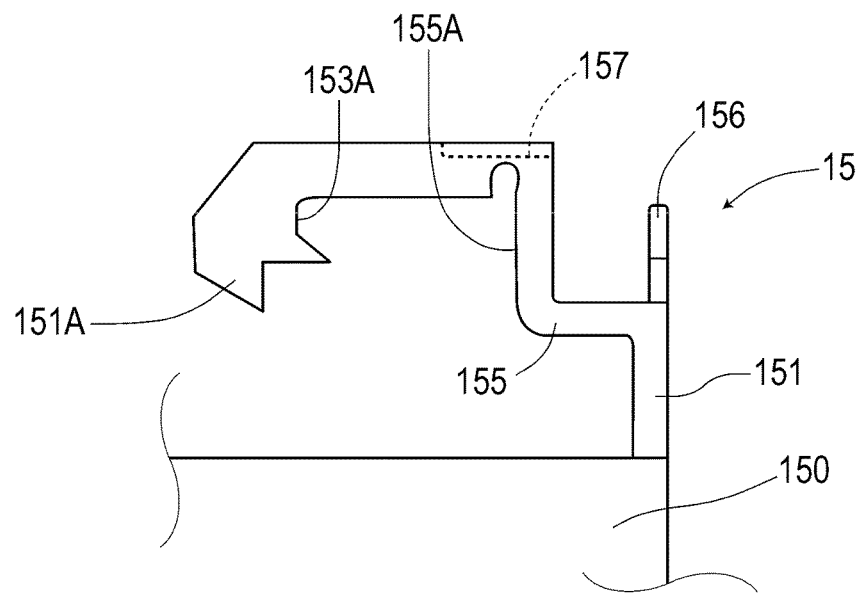
FIG. 9 is a side view showing a holder post being processed according to the first working example.
Figure 10:
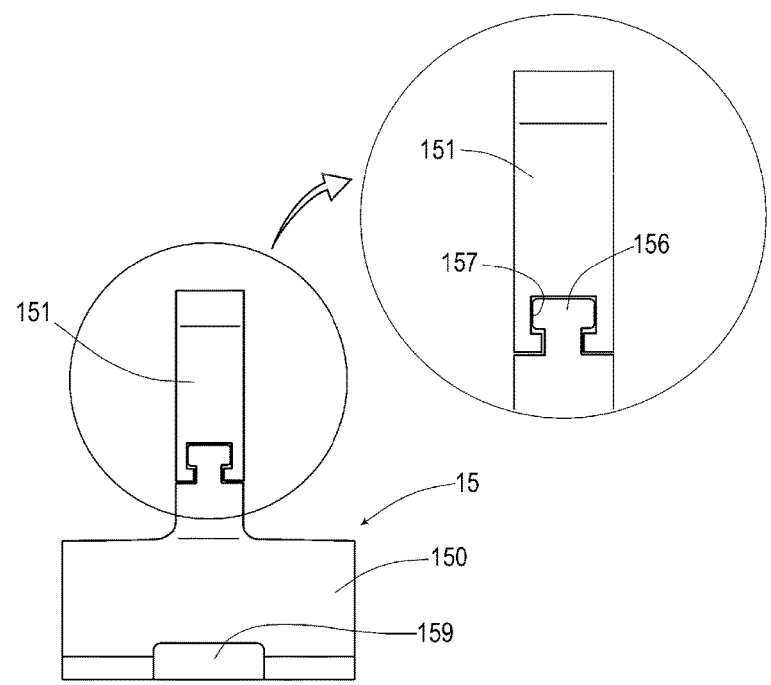
FIG. 10 is a front view showing a holder body according to the first working example.

As shown in FIGS. 9 and 10, the holder post 151 being processed in a state immediately after resin molding has a shape of a hook with the bent part 155 stretched out at a right angle. In the holder post 151, a latch 156 and a catcher 157 are provided at opposite sides of the bent part 155. The latch 156 located at a root side of the holder post 151 axially extends so as to branch off from the bent part 155 formed at a right angle with respect to the axial direction (see FIG. 9). The catcher 157 provided at an outer side surface of the distal end side is a hollow depression to go into engagement with the latch 156. The latch 156 is a projecting strip increased in width at the distal end side thereof. The catcher 157 has a narrow opening formed to be suited to a narrow root portion of the latch 156. A bottom side of the catcher 157 is formed to have a large width. A combination of the latch 156 and the catcher 157 forms a latch mechanism to maintain the hairpin shape of the bent part 155 (see FIG. 7).

Process of completing the holder post 151 is realized by bending the hook-like bent part 155 in FIG. 9 into a hairpin shape. When the bent part 155 is bent into a hairpin shape, the latch 156 is housed in the catcher 157 as shown in FIG. 10 to achieve an engagement structure. This engagement structure maintains the hairpin shape of the bent part 155 reliably.

As shown in FIG. 7, the coil spring (elastic member) 18 is assembled to the holder post 151 with the bent part 155 bent into a hairpin shape. The spring 18 is held between the seats 153A and 155A in a pair while being compressed axially. The holder body 15 holding the spring 18 in this way is assembled to the cap 11 while the clip part 151A is in engagement with the locking part 115.

As shown in FIGS. 4 to 6, the second holder member 12 which is made of polycarbonate, has a shape of a substantial cylinder with a bottom. An attachment portion 125 with a smaller diameter stands on an end surface of the second holder member 12 at the bottom side thereof. This holder member 12 is formed to be smaller in diameter than the opening 230 of the vial 2 (FIG. 3). The attachment portion 125 has a thread formed on the outer circumferential surface thereof so that it can be threaded into the gasket 25. The attachment portion 125 is threaded into the gasket 25 until the end surface of the holder member 12 on which the attachment portion 125 stands is in close contact with the gasket 25. Seats 129 like a flange projecting toward the outer circumferential side are arranged at an opposite open end so as to be in opposition to each other. The seats 129 in a pair in opposition to each other take the place of the seat 155A of the holder member 11A to become new seats of the spring 18 when the injection needle 100A is automatically housed. In FIGS. 4, 6 and other figures, only one of the seats 129 in a pair is shown. The present example can be replaced by a structure of fixing the needle unit 1 to the gasket 25 by press fitting the attachment portion 125 into a hole of the gasket 25.

The inner diameter of a second hollow portion 12H, which is the internal space of the second holder member 12, is set so as to allow the surrounding sleeve 13 (FIG. 6) to be inserted into the second hollow portion 12H. A second slider portion 120 that can hold the retaining member 10 is provided in the second hollow portion 12H. This slider portion 120 is composed of three pillar-shaped parts 121 that extend from the bottom side of the hollow portion 12H along the axial direction (a direction toward the open end).

The three pillar-shaped parts 121 are all formed in accordance with the same specifications as the above-described pillar-shaped parts 111 of the first holder member 11A, and provided at three positions at an equal interval in the circumferential direction similarly to the pillar-shaped parts 111. The three pillar-shaped parts 121 form an inner circumferential space with a substantially circular cross-section. The slider portion 120 holds the retaining member 10 in this inner circumferential space with the pillar-shaped parts 121 circumscribing the outer circumferential surface of the retaining member 10.

When the pillar-shaped parts 111, 121 are arranged alternately in the circumferential direction, they fill the gaps therebetween without overlapping with one another, and therefore form a substantially complete circular ring in cross-section. In the state where the pillar-shaped parts 111, 121 are arranged alternately in the circumferential direction, the holder members 11A, 12 are retractable in the axial direction with the pillar-shaped parts 111, 121 engaging with one another in a comb teeth form.

As shown in FIGS. 4 to 6, the pillar-shaped parts 111, 121 have three types of grooves 111A to 111C, 121A to 121C on the outer circumferential surfaces thereof, and projections 111T, 121T on the inner circumferential surfaces of the distal ends thereof.

Each projection 111T, 121T, which projects toward the inner circumferential side, is formed in one place on the inner circumferential surface of the corresponding pillar-shaped parts 111, 121. The inner diameter formed by projecting surfaces of the three projections 111T, 121T of the holder member 11A, 12 is substantially the same as the outer diameter of the small-diameter portion 105 of the retaining member 10. When the holder member 11A advances/retreats in the axial direction with respect to the retaining member 10, the projections 111T of the first holder member 11A advance/retreat in the advance/retreat grooves 10N in the second shaft portion 10B. When the holder member 12 advances/retreats in the axial direction with respect to the retaining member 10, the projections 121T of the second holder member 12 advance/retreat in the advance/retreat grooves 10M in the first shaft portion 10A.

As shown in FIGS. 4 to 6, the advance/retreat grooves 111A, 121A are grooves that extend axially on the outer circumferential surfaces of the pillar-shaped parts 111, 121 at substantial centers of the pillar-shaped parts 111, 121 in the circumferential direction. These advance/retreat grooves 111A, 121A are formed from just before the proximal ends of the pillar-shaped parts 111, 121 to just before the distal ends of the pillar-shaped parts 111, 121.

In a viewing in which the bottom sides of the holder members 11A, 12 are viewed from the opening sides thereof, tapered grooves 111B, 121B are formed on the left rotation sides of the advance/retreat grooves 111A, 121A. The tapered grooves 111B, 121B extend along the circumferential direction, gradually become deeper toward the left rotation sides, and open to the side surfaces of the pillar-shaped parts 111, 121.

The tapered grooves 111C, 121C are provided along the axial direction on the distal end portions of the pillar-shaped parts 111, 121 where the advance/retreat grooves 111A, 121A are not formed. In the circumferential direction, the positions of the tapered grooves 111C, 121C coincide with the positions of the advance/retreat grooves 111A, 121A. The tapered grooves 111C, 121C gradually become deeper toward the distal end side in the axial direction, and open to the distal end surfaces of the pillar-shaped parts 111, 121.

Figure 11:
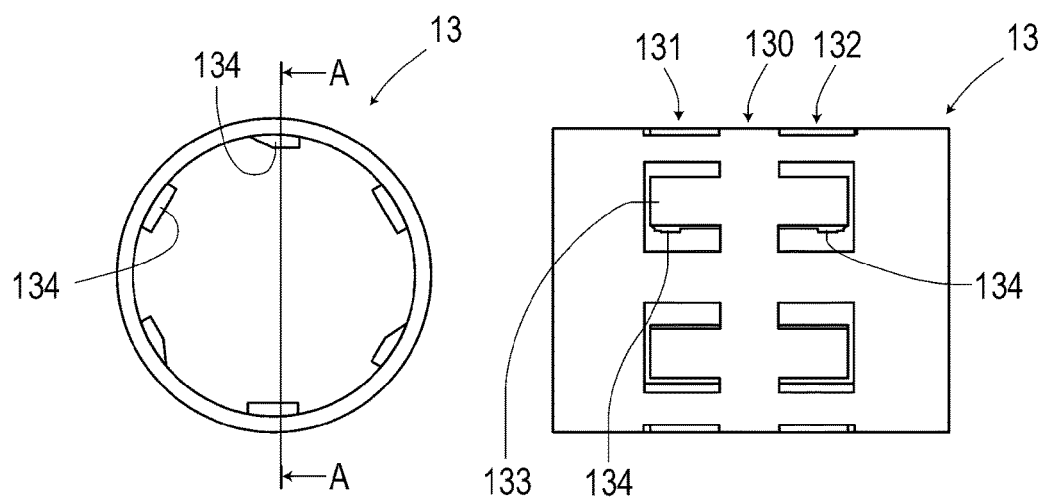
FIG. 11 shows a surrounding sleeve according to the first working example.
Figure 12:
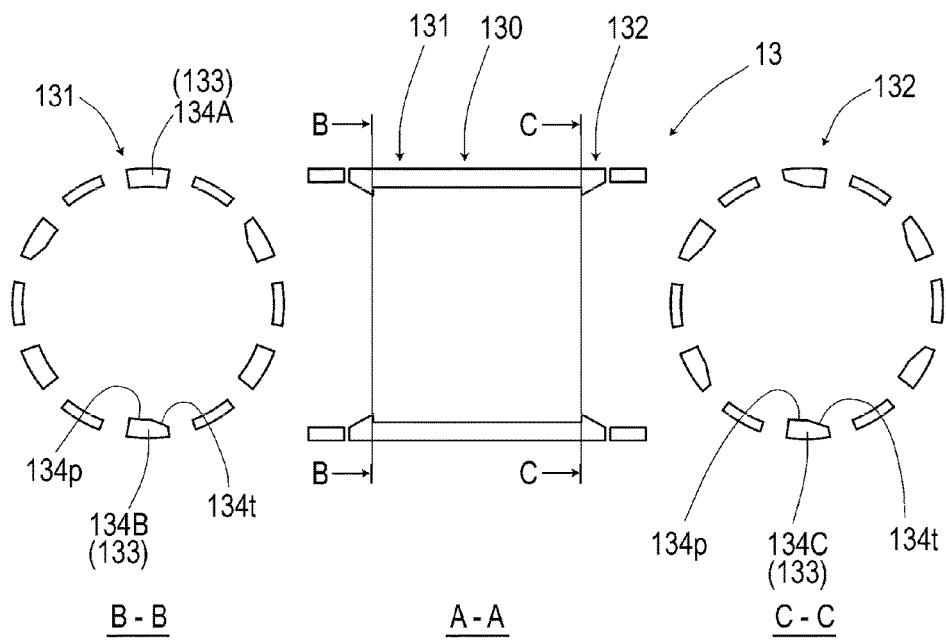
FIG. 12 is a cross-sectional view showing a cross-sectional configuration of the surrounding sleeve according to the first working example.

As shown in FIGS. 6, 11 and 12, the surrounding sleeve 13, which is made of polycarbonate, has a substantially cylindrical shape and is housed in the holder members 11A, while surrounding the slider portions 110, 120. The surrounding sleeve 13 has a first formation portion 131 and a second formation portion 132. With a middle portion 130 serving as the axial center, the first formation portion 131 and the second formation portion 132 are respectively assembled into the first holder member 11A and the second holder member 12. In each of the first formation portion 131 and the second formation portion 132, six lock pieces 133 are provided at a substantially equal interval in the circumferential direction. Each lock piece 133 is formed by cutting the outer circumferential wall of the first formation portion 131 or the second formation portion 132 into a squared-C shape, in such a manner that the root end of each lock piece 133 is located in vicinity to the middle portion 130. In the circumferential direction, the positions at which the lock pieces 133 of the first formation portion 131 are formed substantially coincide with the positions at which the lock pieces 133 of the second formation portion 132 are formed.

As shown in FIGS. 11 and 12, every lock piece 133 has a hook-like part 134 projecting inward at the distal end side thereof (see the A-A cross-section in FIG. 11). The hook-like parts 134 have a substantially wedge-shaped cross-section. More specifically, the height of the hook-like parts 134 in the projecting direction gradually increases toward the middle portion 130.

As shown in FIG. 12, the shape and configuration of these hook-like parts 134 differ between the first formation portion 131 and the second formation portion 132. In the first formation portion 131, there are two types of hook-like parts 134. As shown in the B-B cross-section in FIG. 12, the height of the first hook-like parts 134A in the projecting direction (a direction toward the inside) is substantially constant in the circumferential direction. As shown in the B-B cross-section in FIG. 12, each second hook-like part 134B includes a part 134*p* and an inclined part 134*t*. The height of the part 134*p* in the projecting direction (the direction toward the inside) is substantially constant in the circumferential direction. The height of the inclined part 134*t* in the projecting direction gradually decreases in the circumferential direction. In each second hook-like part 134B of the first formation portion 131, the inclined part 134*t* is arranged at the left rotation side in the B-B cross-section in FIG. 12.

The hook-like parts 134C of the second formation portion 132 are all formed in accordance with the same specifications as shown in FIG. 12. As shown in a C-C cross-section in FIG. 12, each hook-like part 134C includes a part 134*p* and an inclined part 134*t*. The height of the part 134*p* in the projecting direction (the direction toward the inside) is substantially constant. The height of the inclined part 134*t* in the projecting direction gradually decreases in the circumferential direction. Similarly to the second hook-like parts 134B of the first formation portion 131, in each hook-like part 134C of the second formation portion 132, the inclined part 134*t* is arranged at the left rotation side in the C-C cross-section in FIG. 12. When assembling the holder members 11A, 12 with respect to the surrounding sleeve 13, the hook-like parts 134 are inserted in the advance/retreat grooves 111A, 121A after climbing over in the axial direction by using the tapered grooves 111C, 121C (see FIG. 6) provided in the holder members 11A, 12.

In the pre-filled syringe 1A (manufactured state) according to the present example with the above-described component configurations, the attachment portion 125 of the second holder member 12 is threaded into the gasket 25 and fixed to the vial 2 (see FIG. 1). The first holder member 11A holds the retaining member 10 with the projections 111T circumscribing the small-diameter portion 105. The second holder member 12 holds the retaining member 10 with the projections 121T circumscribing the small-diameter portion 105. The first holder member 11A and the second holder member 12 are coaxially joined via the retaining member 10. More specifically, the first holder member 11A and the second holder member 12 are joined via the retaining member 10 in such a manner that the slider portions 110, 120 (pillar-shaped parts 111, 121) thereof do not overlap with one another in the axial direction (see FIG. 5). Furthermore, the surrounding sleeve 13 is arranged around the outer circumferences of the slider portions 110, 120 of the first and second holder members 11A, (see FIG. 6).

Figure 13:
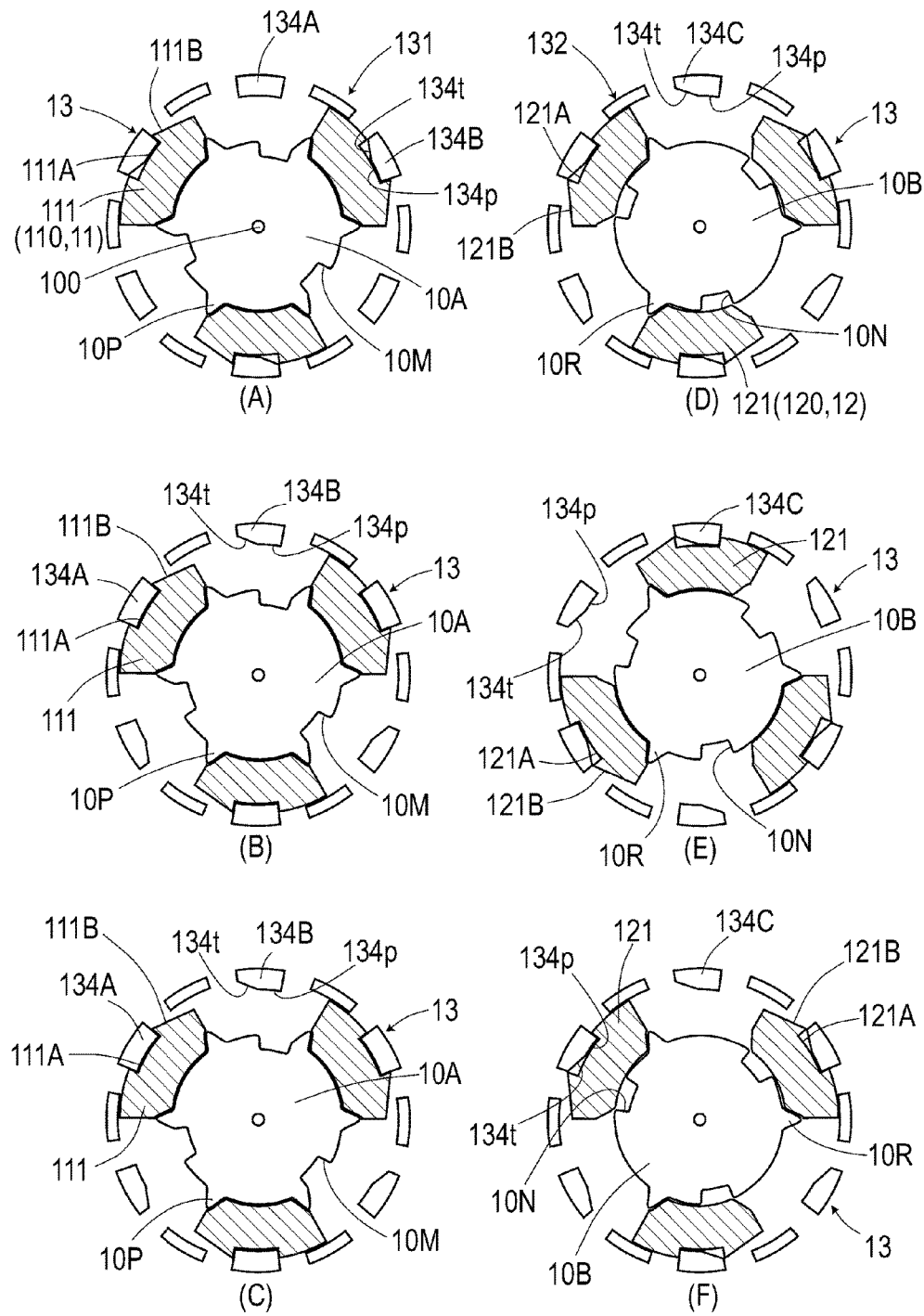
FIG. 13 is explanatory views showing operations of the needle unit according to the first working example.
Figure 14:
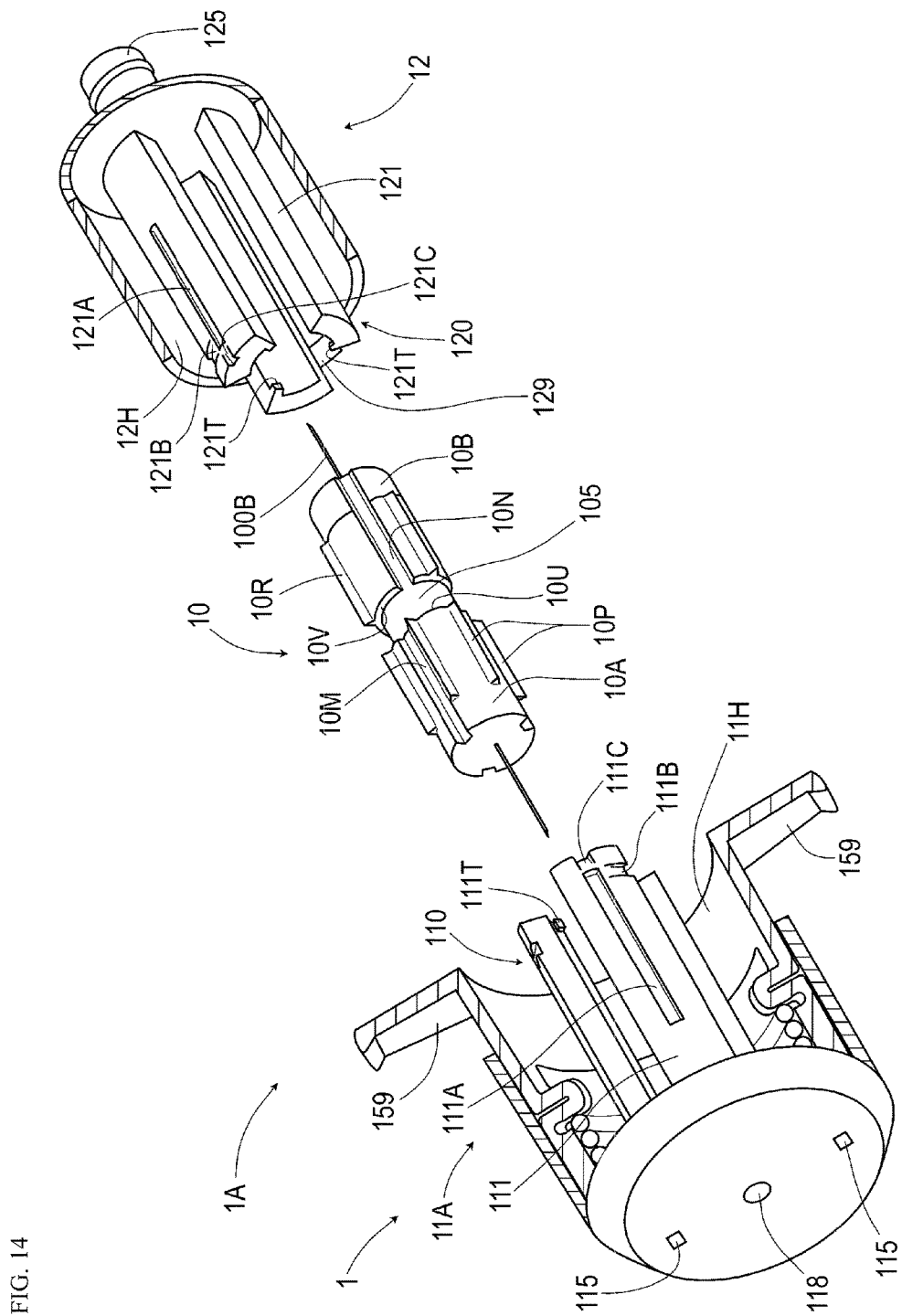
FIG. 14 is a perspective view showing the assembly configuration of the needle unit in the injection state according to the first working example.
Figure 15:
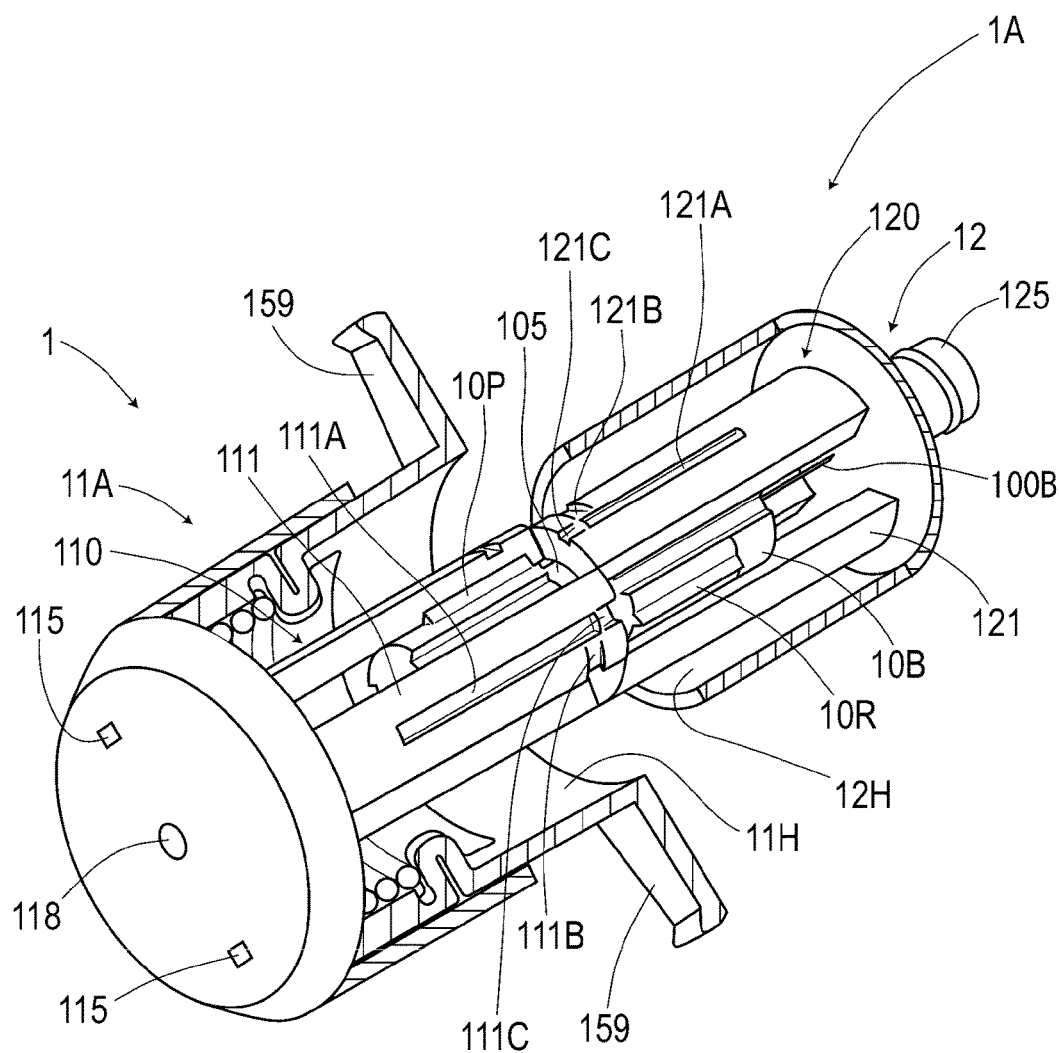
FIG. 15 is a perspective view showing the needle unit in an axially retractable state according to the first working example.
Figure 16:
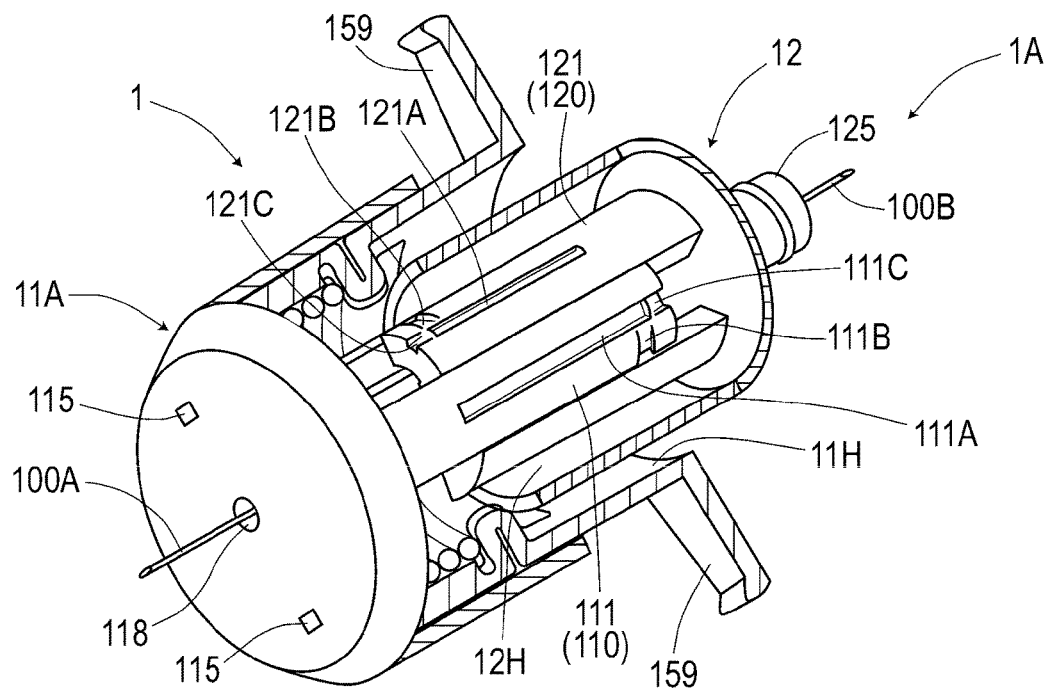
FIG. 16 is a perspective view showing the needle unit in the injection state according to the first working example.

The slider portions 110, 120, the surrounding sleeve 13, and the retaining member in the manufactured state are arranged as shown in FIGS. 13(A) and 13(D) in the uppermost row in FIG. 13. Note that in this FIG. 13, FIGS. 13(A) to 13(C) in the left column are cross-sectional views showing cross-sections including the tapered grooves 111B in the first holder member 11A as viewed from the distal end side of the pre-filled syringe 1A. In this FIG. 13, FIGS. 13(D) to 13(F) in the right column are cross-sectional views showing cross-sections including the tapered grooves 121B in the second holder member 12 as viewed from the distal end side of the pre-filled syringe 1A. FIGS. 13(A) to 13(C) show cross-sections of the first formation portion 131 in the surrounding sleeve 13, the slider portion 110 in the holder member 11A, and the first shaft portion 10A in the retaining member 10, from the outer circumferential side. FIGS. 13(D) to 13(F) show cross-sections of the second formation portion 132 in the surrounding sleeve 13, the slider portion 120 in the holder member 12, and the second shaft portion 10B in the retaining member 10, from the outer circumferential side.

As shown in FIGS. 13(A) and 13(D) in FIG. 13, in the pre-filled syringe 1A in the manufactured state, the positions of the pillar-shaped parts 111 in the first holder member 11A substantially coincide with the positions of the pillar-shaped parts 121 in the second holder member 12 in the circumferential direction (see FIG. 5). In this state, the pre-filled syringe 1A is in the axially non-retractable state as the distal end surfaces of the pillar-shaped parts 111 face the distal end surfaces of the pillar-shaped parts 121. The retaining member is completely housed in the first and second holder members 11A, 12, and the injection needle 100A at the distal end side and the perforation needle 100B at the side of the vial 2 are stowed as well (see FIG. 1).

As shown in FIG. 13(A) in FIG. 13, the outer circumferential surface of the first shaft portion 10A in the retaining member 10 is segmented into six surface regions in the circumferential direction by the ridge portions 10P; out of these six surface regions, surface regions where the advance/retreat grooves 10M are not formed are circumscribed by the pillar-shaped parts 111 in the first holder member 11A. A rotation of the first holder member 11A relative to the retaining member 10 is restricted by the ridge portions 10P provided at six places in the circumferential direction. The second hook-like parts 134B of the surrounding sleeve 13 (first formation portion 131) are inserted in the advance/retreat grooves 111A in the pillar-shaped parts 111. As described above, the inclined parts 134t are formed on these second hook-like parts 134B at the left rotation sides in FIG. 13(A).

On the other hand, as shown in FIG. 13(D) in FIG. 13, the outer circumferential surface of the second shaft portion 10B in the retaining member 10 is segmented into three surface regions by the ridge portions 10R; these three surface regions are each circumscribed by the corresponding pillar-shaped part 121 in the second holder member 12. In FIG. 13(D), the second holder member 12 has completely rotated toward the right rotation side with respect to these three surface regions that each span across approximately 120 degrees in the circumferential direction. The hook-like parts 134C in the surrounding sleeve 13 (second formation portion 132) are inserted in the advance/retreat grooves 121A provided on the outer circumferential surfaces of the pillar-shaped parts 121. As described above, the inclined parts 134t are formed on these hook-like parts 134C at the left rotation sides in FIG. 13(D).

The use of the pre-filled syringe 1A according to the present example will now be described. In order to inject the pre-filled syringe 1A, the second holder member 12 is rotated with respect to the first holder member 11A and the retaining member 10 by 60 degrees in the left rotation direction in FIG. 13. The width of each pillar-shaped part 121 in the second holder member 12 in the circumferential direction is equivalent to approximately 60 degrees in the circumferential direction. On the other hand, as shown in FIG. 13(D), in the second shaft portion 10B of the retaining member circumscribed by the pillar-shaped parts 121, the ridge portions 10R are provided in three places at a substantially equal interval in the circumferential direction, so as to segment the outer circumferential surface into surface regions that each span across approximately 120 degrees in the circumferential direction. In the state where the pillar-shaped parts 121 circumscribe the second shaft portion 10B in the retaining member 10, the second holder member 12 is rotatable relative to the retaining member 10 within a range of approximately 60 degrees. A leftward rotation of the second holder member 12 causes the surrounding sleeve 13 to rotate leftward due to the engagement between the advance/retreat grooves 121A and the hook-like parts 134C.

As shown in FIG. 13(A), on the second hook-like parts 134B that engage with the advance/retreat grooves 111A in the first slider portion 110, the inclined parts 134t are formed at the left rotation sides. Furthermore, the tapered grooves 111B extending along the circumferential direction are formed in the pillar-shaped parts 111 at the right rotation sides. When the surrounding sleeve 13 is caused to rotate leftward by the leftward rotation of the second holder member 12 as described above, the second hook-like parts 134B exit the advance/retreat grooves 111A by using the inclined parts 134t, and the first hook-like parts 134A climb into the advance/retreat grooves 111A by using the inclined bottom surfaces of the tapered grooves 111B, as shown in FIGS. 13(A) and 13(B).

When the second holder member 12 is rotated leftward together with the surrounding sleeve 13 in the above-described manner, an injection state of FIGS. 13(B) and 13(E) can be realized. In this injection state, the pillar-shaped parts 111 of the first holder member 11A and the pillar-shaped parts 121 of the second holder member 12 are positioned alternately in the circumferential direction. In the state where the pillar-shaped parts 111, 121 are thus arranged alternately, the needle unit 1 is retractable in the axial direction (see FIGS. 14 to 16).

For example, first, the needle unit 1 is retracted in the axial direction with a pointing finger and a middle finger placed around the finger grips 159 and a thumb placed on a bottom surface 210 of the vial 2 (see FIG. 2). Once the needle unit 1 has been retracted in the axial direction to the extent that the length thereof in the axial direction is shorter than the total length of the retaining member 10 inclusive of the injection needle 100A and the perforation needle 100B, the perforation needle 100B projects from the attachment portion 125 of the second holder member 12, and the injection needle 100A projects from the distal end of the first holder member 11A. The perforation needle 100B penetrates through the wall 251 in the gasket 25 (see FIG. 3), and the distal end thereof reaches the inside of the vial 2. When the needle unit 1 is retracted in the axial direction to the fullest extent, the injection needle 100A and the perforation needle 100B project to the fullest extent. By pushing the needle unit 1 toward the bottom side of the vial 2, the pre-filled syringe 1A is further retracted in the axial direction, and the gasket 25 moves in the forward direction. This enables injection of the drug solution.

As shown in FIG. 13(B), in the pre-filled syringe 1A in the injection state, the first hook-like parts 134A of the surrounding sleeve 13 (first formation portion 131) are inserted in the advance/retreat grooves 111A in the first slider portion 110. Furthermore, as shown in FIG. 13(E) in FIG. 13, the second holder member 12 has completely rotated toward the left rotation side with respect to the outer circumferential surface that is segmented by the ridge portions 10R into surface regions that each span across 120 degrees in the circumferential direction. As the leftward rotation of the second holder member 12 causes the surrounding sleeve 13 to rotate from the state of FIG. 13(D) to the state of FIG. 13(E) in FIG. 13, the hook-like parts 134C inserted in the advance/retreat grooves 121A in the second slider portion 120 are not switched. During the post-injection handling, the inclined parts 134t that are provided in these hook-like parts 134C in the left rotation sides achieve extremely important operational effects.

Figure 17:
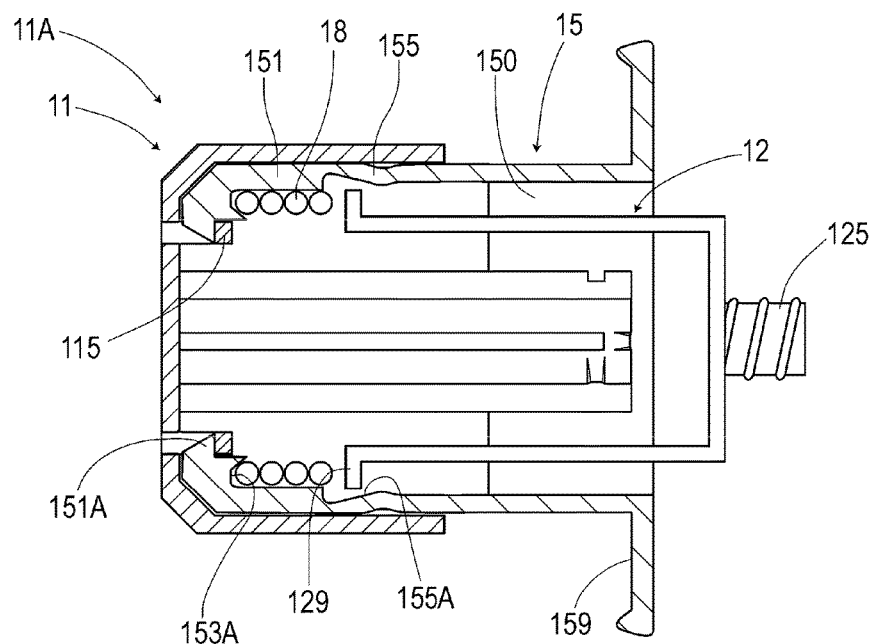
FIG. 17 is a cross-sectional view showing a state where a bent part of the first holder member extends according to the first working example.

The following describes process to be performed after injection with the pre-filled syringe 1A of the present example. After the injection, pushing in the vial 2 further toward the needle unit 1 pulls the latch 156 out of the catcher 157 (see FIG. 10) of the first holder member 11A, thereby stretching the bent part 155. This releases restriction on the spring 18 having been maintained in a compressed state by the first holder member 11A, so that an end portion of the spring 18 close to the bent part 155 is pushed against the seat 129 of the second holder member 12. In FIG. 17, to place importance on ease of understanding, the slider portion 120 of the second holder member 12, the surrounding sleeve 13, the latch 156 and others are omitted and the position of the seat 129 in the circumferential direction is changed. The seat 129 is actually located at a position separated by about 90 degrees from the bent part 155 in the circumferential direction.

The biasing force of the spring 18 acts to extend the needle unit 1 in the axial direction. The needle unit 1 extends until the hook-like parts 134A of the surrounding sleeve reach respective terminal ends of the advance/retreat grooves 111A in the first slider portion 110 and until the hook-like parts 134C reach respective terminal ends of the advance/retreat grooves 121A in the second slider portion 120. Extension of the needle unit 1 in the axial direction is also restricted by engagement of the projections 111T and 121T of the pillar-shaped parts 111 and 121 with the end surfaces 10U and 10V of the retaining member 10. This reliably restricts the maximum extension positions of the holder members 11A and 12.

After extending the needle unit 1 in the axial direction in the above-described manner, the second holder member 12 is rotated by 60 degrees in the right rotation direction in FIG. 13. At this time, as described above, hook-like parts that are inserted in the advance/retreat grooves 111A in the first slider portion 110 are the first hook-like parts 134A with no inclined parts 134t (FIG. 13(B) in FIG. 13). These first hook-like parts 134A cannot exit the advance/retreat grooves 111A even with the occurrence of a rotational force relative to the first holder member 11A. Therefore, in the state of FIG. 13(B) in FIG. 13, a relative rotation of the first holder member 11A and the surrounding sleeve 13 is restricted.

On the other hand, as shown in FIG. 13(E), in the hook-like parts 134C inserted in the advance/retreat grooves 121A in the second slider portion 120, the inclined parts 134t are formed at the left rotation sides. Therefore, a rightward rotation of the second holder member allows the hook-like parts 134C to exit the advance/retreat grooves 121A by using the inclined parts 134t. When the second holder member 12 is rotated rightward relative to the surrounding sleeve 13, the second slider portion 120 approaches new hook-like parts 134C. As all the hook-like parts 134C include the inclined parts 134t at the left rotation sides, they can climb into the advance/retreat grooves 121A in the slider portion 120 by using these inclined parts 134t. Therefore, when the second holder member 12 is rotated rightward in the state of FIG. 13(E), only the second holder member 12 can be rotated rightward without causing the surrounding sleeve 13 to rotate.

The aforementioned rightward rotation of the second holder member 12 in the injection state of FIGS. 13(B) and 13(E) leads to a disposal state shown in FIGS. 13(C) and 13(F) in FIG. 13. In this disposal state, the positions of the pillar-shaped parts 111 in the first holder member 11A substantially coincide with the positions of the pillar-shaped parts 121 in the second holder member 12 in the circumferential direction. That is to say, in this state, the pre-filled syringe 1A is in the axially non-retractable state as the distal end surfaces of the pillar-shaped parts 111 face the distal end surfaces of the pillar-shaped parts 121.

As shown in FIG. 13(C), the first hook-like parts 134A with no inclined parts 134t are inserted in the advance/retreat grooves 111A in the first slider portion 110. Therefore, in this state, the surrounding sleeve 13 cannot be rotated relative to the first holder member 11A. Furthermore, as six ridge portions 10P are formed on the outer circumference of the first shaft portion 10A, the first holder member 11A cannot be rotated relative to the retaining member 10, either.

As shown in FIG. 13(F), the hook-like parts 134C, which have the inclined parts 134t on the left rotation sides, are inserted in the advance/retreat grooves 121A in the second slider portion 120. In FIG. 13(F), a leftward rotation of the second holder member 12 is restricted due to the engagement between the advance/retreat grooves 121A and the hook-like parts 134C, and a rightward rotation of the second holder member 12 is restricted by the ridge portions 10R with which the right rotation sides of the pillar-shaped parts 121 are in contact. Therefore, the second holder member 12 cannot be rotated relative to the retaining member 10.

As described above, upon shifting to the states of FIGS. 13(C) and 13(F) by rotating the second holder member 12 rightward after use, the action of a rotation restriction mechanism made up of the surrounding sleeve 13 and the like does not allow a relative rotation of the first holder member 11A and the second holder member 12.

Furthermore, in the state of FIG. 13(C), the positions of the advance/retreat grooves 10M in the first shaft portion 10A and the positions of the projections 111T in the first holder member 11A differ in the circumferential direction. In this way, the projections 111T engage with the end surface 10U between the small-diameter portion 105 and the first shaft portion 10A, thereby restricting withdrawal of the first holder member 11A from the retaining member 10 in the axial direction. Similarly, in the state of FIG. 13(F), the positions of the advance/retreat grooves 10N in the second shaft portion 10B differ from the positions of the projections 121T in the second holder member 12 in the circumferential direction. In this way, the projections 121T engage with the end surface 10V between the small-diameter portion 105 and the second shaft portion 10B, thereby restricting withdrawal of the second holder member 12 from the retaining member 10 in the axial direction.

The pre-filled syringe 1A of the present example having the aforementioned structure is a very compact syringe of a high level of safety. The pre-filled syringe 1A is an excellent product that can considerably save effort required for injection and can place the injection needle 100A in a housed state with a single touch after the injection.

The latch mechanism of the bent part 155 realized by the combination of the latch 156 and the catcher 157 of the present example may be replaced for example by a latch mechanism realized by a combination of a mushroom-shaped projection and a recess, or by a latch mechanism such as Ziploc (registered trademark) realized by a combination of a projecting rail having a spreading out shape in cross section and a recessed groove to house this rail. The latch mechanism of the present example is employed with the intention of maintaining the hairpin shape of the bent part 155 (see FIG. 7). This latch mechanism can be replaced by a rupture mechanism. According to an example of the applicable rupture mechanism, the distal end of the latch 156 is joined (by adhesive contact or welding, for example) to the catcher 157 and a portion of the latch 156 corresponding to a root thereof is made rupturable. According to another example of the applicable rupture mechanism, opposite sides of the distal end of the latch 156 rupture to be pulled out of the catcher 157.

In the present example, restriction on the spring 18 is released in response to deformation of the bent part 155 forming the seat 155A. Instead, restriction on the spring can also be released for example by a structure of deforming the seat 155A by making the seat 155A rupture or cutting the seat 155A in response to push-in after injection, or a structure of elastically displacing (retreating, for example) the seat 155A in response to push-in.

In the present example, the seat 129 of the second holder member 12 is provided to become a new seat after restriction on the spring 18 is released. Instead, the second holder member 12 may be biased indirectly by pushing an end portion of the spring 18 after recovering elasticity against the vial 2.

Second Working Example

Figure 18:
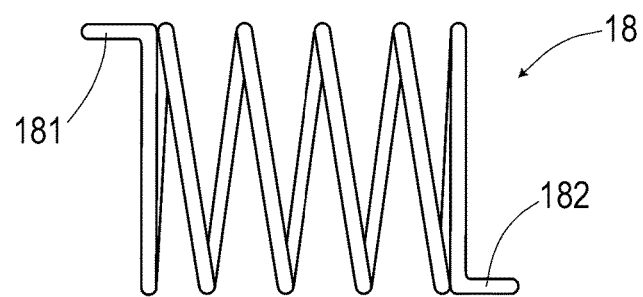
FIG. 18 is a side view of a spring according to a second working example.

The present example is based on the pre-filled syringe of the first working example. The present example facilitates automation of action to be taken after injection. Specifics of this pre-filled syringe will be described below with reference to FIG. 18.

The pre-filled syringe of the present example differs from the spring of the first working example. A spring 18 of the present example is prohibited from rotating while being turned in a rotation direction and is held by the first holder member 11A in this state. The spring 18 has projecting ends 181 and 182 axially projecting at its opposite ends formed by bending winding ends of the spring 18. The projecting ends 181 and 182 are prohibited from rotating while in engagement with side surfaces of the seats 153A and 155A. The rotation direction where the spring 18 is turned corresponds to a direction where rotation elastic force is accumulated to be applied to bias the second holder member 12 in the right rotation direction in FIG. 13.

Push-in performed after injection releases restriction on the spring 18. This makes an end portion of the spring 18 abut on the seat 129 of the second holder member 12 and makes the projecting end 182 engage a side surface of the seat 129. Thus, the aforementioned rotation elastic force is partially or entirely maintained as it is. If the needle unit 1 extends to a position that allows the second holder member 12 to rotate relative to the first holder member 11A, the second holder member 12 is biased by the spring storing the rotation elastic force to rotate in the right rotation direction in FIG. 13.

This right rotation corresponds to the 60-degree right rotation (FIG. 13) of the second holder member 12 in the needle unit 1 to occur after injection described in the first working example.

The present example has the same structure and achieves the same operational effects as those of the first working example.

Third Working Example

Figure 19:
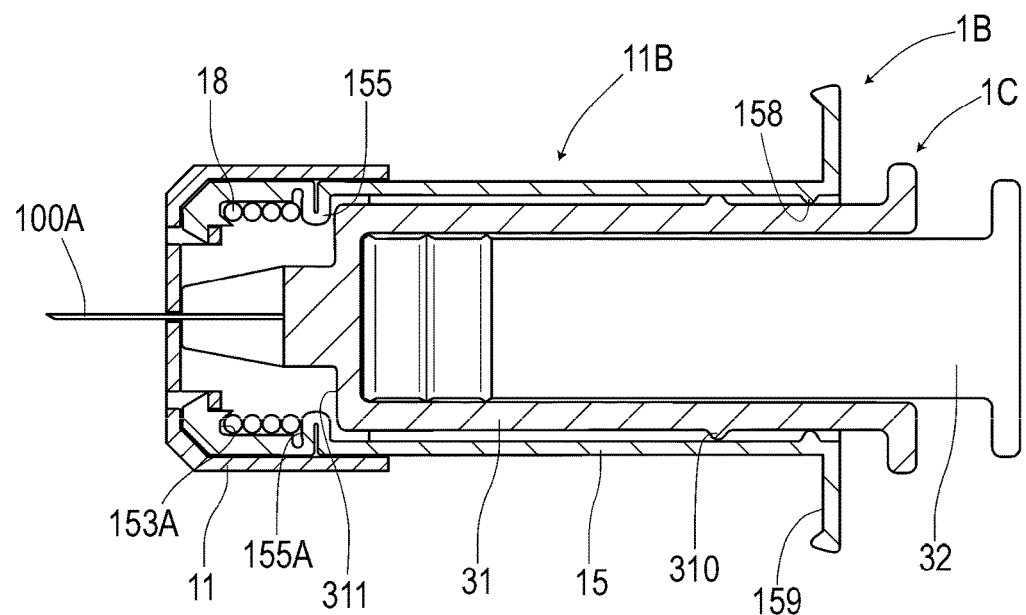
FIG. 19 is a cross-sectional view showing a cross-sectional configuration of a syringe taken during injection according to a third working example.
Figure 20:
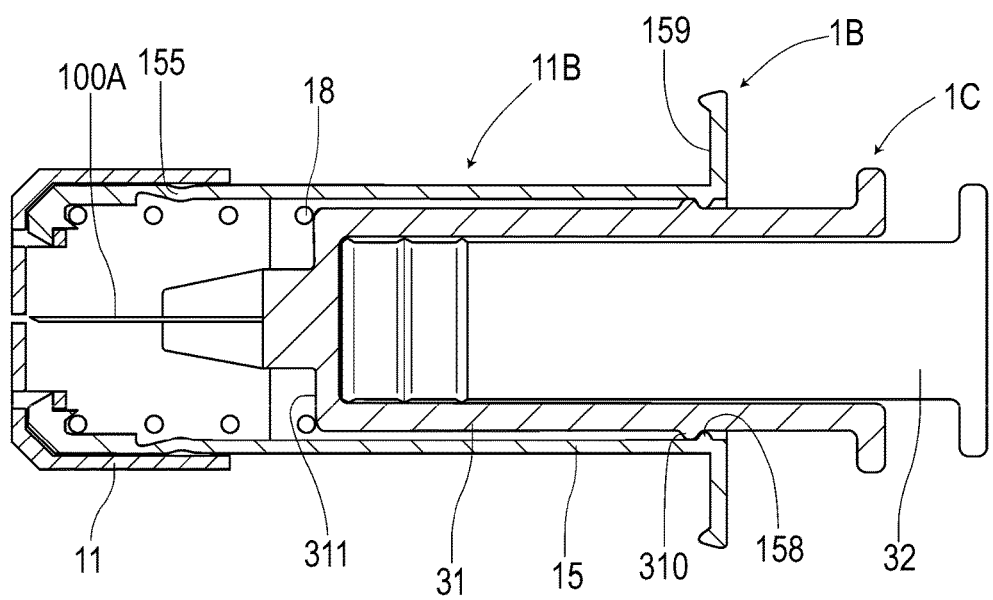
FIG. 20 is a cross-sectional view showing a cross-sectional configuration of the syringe with an injection needle being housed.

The present example describes an example of a syringe 1B employing a needle cover as an application of the first holder member of the first working example. Specifics of this syringe will be described below with reference to FIGS. 19 and 20.

The needle cover 11B of the present example is a member formed by removing a slider portion (symbol 110 in FIG. 7) from the first holder member (symbol 11A in FIG. 7) of the first working example, extending the resultant first holder member in the axial direction, and providing a fall prevention portion 158 to the inner circumferential surface at an open end. A syringe body 1C to be combined with the needle cover 11B is a syringe used for injecting a drug solution in a solution chamber by pushing a plunger (operational part) 32 into an injection cylinder 31. A projecting portion 310 responsive to the fall prevention portion 158 is provided in the outer circumferential surface of the injection cylinder 31.

A drug solution can be injected by pushing in the plunger 32 with fingers placed around the finger grips 159 of the needle cover 11B. By pushing in the plunger 32 further after the injection, the bent part 155 is deformed to be substantially flattened. Thus, restriction on the spring 18 is released to make the spring abut on a distal end surface 311 of the injection cylinder 31 (see FIG. 20). This makes the needle cover 11B move forward to house the injection needle 100A.

The present example has the same structure and achieves the same operational effects as those of the first working example.

The invention claimed is:

1. A syringe, comprising:
a syringe body including an injection needle, a solution chamber storing a drug solution, and an operational part to be operated in a certain direction to inject the drug solution stored in the solution chamber from the injection needle;
a cylindrical needle cover housing the injection needle; and
an elastic member held by the needle cover while being compressed in an axial direction of the injection needle, wherein
the needle cover has seats in a pair to restrict the positions of both end portions of the elastic member in the axial direction by making abutting contact with the both end portions of the elastic member, before injection, the elastic member being held in a gap between the seats in a pair, and one of the seats in a pair being a deformable seat,
the deformable seat of the seats in a pair is deformed in response to operation on the operational part in the certain direction performed after injection, so that the deformable seat is unable to restrict the position of the one end portion of the elastic member and the one end portion of the elastic member, which is released from the deformable seat, moves in the axial direction beyond the position of the deformable seat, which is deformed after injection,
the syringe body has a seat portion, on which none of the end portions of the elastic member abuts before injection and the one end portion of the elastic member does not abut until the deformable seat is deformed, and
in response to deformation of the deformable seat, the one end portion of the elastic member is released from the deformed seat and then abuts on the seat portion of the syringe body to move the needle cover in a direction away from the syringe body, the injection needle is covered by the needle cover.

2. The syringe according to claim 1, wherein
the deformable seat is formed of a bent part of a substantial hairpin shape projecting toward an inner circumferential side of the needle cover and the bent part is deformed by stretching so as to be substantially flattened, and
the elastic member is released from the restriction on the position of the one end portion of the bent part in response to the deformation of the bent part.

3. The syringe according to claim 2, wherein the deformable seat has a latch mechanism that maintains holding of the bent part until injection is finished, and releases the bent part from the holding when the operational part is operated in the certain direction after the injection.

4. A syringe, comprising:
a drug solution container that is filled with a drug solution and has a shape of a cylinder with a bottom;
a closing member that closes an opening of the drug solution container in a manner movable in a boring direction of the cylindrical shaped drug solution container; and
a needle housing unit that is attached to the closing member so as to allow the closing member to be pushed into the drug solution container, wherein
the needle housing unit includes:
a substantially columnar retaining member with an injection needle projecting from one end thereof and a perforation needle projecting from the other end thereof;

a first holder member provided with a first hollow portion having a bottom and with a first slider portion, the first slider portion holding the retaining member using at least two pillar-shaped parts, the at least two pillar-shaped parts extending from a bottom side of the first hollow portion along an opening direction of the first hollow portion, which is equivalent to an axial direction of the injection needle, the at least two pillar-shaped parts circumscribing an outer circumferential surface of the retaining member, the first holder member, provided with seats in a pair at two positions in the axial direction, holding an elastic member in a compressed state with each position of both end portions in the axial direction restricted by a corresponding seat of the seats in a pair;

a second holder member provided with a second hollow portion having a bottom, with a second slider portion, and with an attachment portion, the second slider portion holding the retaining member using at least two pillar-shaped parts, the at least two pillar-shaped parts extending from a bottom side of the second hollow portion along an opening direction of the second hollow portion, which is equivalent to the axial direction, the at least two pillar-shaped parts circumscribing the outer circumferential surface of the retaining member, the attachment portion being provided so as to extend along a bottom end of the second holder member for the closing member, the first holder member and the second holder member are rotatable relative to each other around the retaining member in a state where each pillar-shaped part in the first slider portion or the second slider portion holding the retaining member does not overlap with any of the pillar-shaped parts in the other slider portion in the axial direction, in a state where the pillar-shaped parts in the first slider portion and the second slider portion are arranged alternately around the retaining member, the first holder member and the second holder member are retractable in the axial direction through insertion of one of the holder members into the hollow portion in the other holder member, whereas in a state where distal end surfaces of the pillar-shaped parts in one of the first slider portion and the second slider portion face distal end surfaces of the pillar-shaped parts in the other slider portion, the first holder member and the second holder member are not retractable in the axial direction, when the first holder member and the second holder member holding the retaining member are retracted in the axial direction, the perforation needle penetrates through the closing member and projects inside the drug solution container, and the injection needle projects toward the outside, when the first holder member and the second holder member are retracted further in the axial direction after injection, a seat being one of the seats in a pair provided in the first holder member is deformed to release restriction on the position of one end portion of the elastic member, and the one end portion of the elastic member abuts on the second holder member directly or indirectly in response to the deformation of the seat, thereby extending the first holder member and the second holder member in the axial direction so as to house the injection needle.

5. The syringe according to claim 4, wherein
the seat is formed of a bent part of a substantial hairpin shape projecting toward an inner circumferential side of the first holder member and the bent part is deformed by stretching so as to be substantially flattened, and the elastic member is released from the restriction on the position of the one end portion in response to the deformation of the bent part.

6. The syringe according to claim 5, wherein the seat has a latch mechanism that maintains holding of the bent part until injection is finished, and releases the bent part from the holding when an operational part is operated in a certain direction after the injection.

7. The syringe according to claim 4, wherein
after injection, the needle housing unit can be placed in the axially non-retractable state again by rotating the first holder member and the second holder member relative to each other after extending the first holder member and the second holder member in the axial direction to positions where each pillar-shaped part in the first slider portion or the second slider portion does not overlap with any of the pillar-shaped parts in the other slider portion in the axial direction, and the elastic member is a spring formed by winding a linear material for a spring into a coil shape, the elastic member is held by the first holder member while storing rotation elastic force to act in a rotation direction generated by turning the elastic member in a circumferential direction, if the elastic member is released from the restriction on the position of the one end portion, the elastic member abuts on a seat provided in the second holder member while storing the rotation elastic force entirely or partially, and the elastic member shifts the needle housing unit into an axially non-retractable state by extending the first holder member and the second holder member in the axial direction until the first holder member and the second holder member become rotatable relative to each other and then by applying the rotation elastic force to rotate the first holder member and the second holder member relative to each other.

8. The syringe according to claim 7, further comprising a surrounding sleeve having a substantially cylindrical shape, the surrounding sleeve restricting a relative rotation of the first holder member and the second holder member around the retaining member in a state where the surrounding sleeve surrounds the first slider portion and the second slider portion, wherein the needle housing unit is in the axially non-retractable state in a manufactured state, and can be placed in the axially retractable state by rotating the first holder member and the second holder member relative to each other around the retaining member during injection, and the surrounding sleeve allows the relative rotation of the first holder member and the second holder member around the retaining member in the manufactured state, and restricts the relative rotation of the first holder member and the second holder member once the needle housing unit has shifted from the axially retractable state to the axially non-retractable state again after injection.

9. The syringe according to claim 5, wherein
after injection, the needle housing unit can be placed in the axially non-retractable state again by rotating the first holder member and the second holder member relative to each other after extending the first holder member and the second holder member in the axial direction to positions where each pillar-shaped part in the first slider portion or the second slider portion does not overlap with any of the pillar-shaped parts in the other slider portion in the axial direction, and the elastic member is a spring formed by winding a linear material for a spring into a coil shape, the elastic member is held by the first holder member while storing rotation elastic force to act in a rotation direction generated by turning the elastic member in a circumferential direction, if the elastic member is released from the restriction on the position of the one end portion, the elastic member abuts on a seat provided in the second holder member while storing the rotation elastic force entirely or partially, and the elastic member shifts the needle housing unit into an axially non-retractable state by extending the first holder member and the second holder member in the axial direction until the first holder member and the second holder member become rotatable relative to each other and then by applying the rotation elastic force to rotate the first holder member and the second holder member relative to each other.

10. The syringe according to claim 9, further comprising a surrounding sleeve having a substantially cylindrical shape, the surrounding sleeve restricting a relative rotation of the first holder member and the second holder member around the retaining member in a state where the surrounding sleeve surrounds the first slider portion and the second slider portion, wherein the needle housing unit is in the axially non-retractable state in a manufactured state, and can be placed in the axially retractable state by rotating the first holder member and the second holder member relative to each other around the retaining member during injection, and the surrounding sleeve allows the relative rotation of the first holder member and the second holder member around the retaining member in the manufactured state, and restricts the relative rotation of the first holder member and the second holder member once the needle housing unit has shifted from the axially retractable state to the axially non-retractable state again after injection.

11. The syringe according to claim 6, wherein after injection, the needle housing unit can be placed in the axially non-retractable state again by rotating the first holder member and the second holder member relative to each other after extending the first holder member and the second holder member in the axial direction to positions where each pillar-shaped part in the first slider portion or the second slider portion does not overlap with any of the pillar-shaped parts in the other slider portion in the axial direction, and the elastic member is a spring formed by winding a linear material for a spring into a coil shape, the elastic member is held by the first holder member while storing rotation elastic force to act in a rotation direction generated by turning the elastic member in a circumferential direction, if the elastic member is released from the restriction on the position of the one end portion, the elastic member abuts on a seat provided in the second holder member while storing the rotation elastic force entirely or partially, and the elastic member shifts the needle housing unit into an axially non-retractable state by extending the first holder member and the second holder member in the axial direction until the first holder member and the second holder member become rotatable relative to each other and then by applying the rotation elastic force to rotate the first holder member and the second holder member relative to each other.

12. The syringe according to claim 11, further comprising a surrounding sleeve having a substantially cylindrical shape, the surrounding sleeve restricting a relative rotation of the first holder member and the second holder member around the retaining member in a state where the surrounding sleeve surrounds the first slider portion and the second slider portion, wherein the needle housing unit is in the axially non-retractable state in a manufactured state, and can be placed in the axially retractable state by rotating the first holder member and the second holder member relative to each other around the retaining member during injection, and the surrounding sleeve allows the relative rotation of the first holder member and the second holder member around the retaining member in the manufactured state, and restricts the relative rotation of the first holder member and the second holder member once the needle housing unit has shifted from the axially retractable state to the axially non-retractable state again after injection.

* * * * *